(12) United States Patent
Mueller et al.

(10) Patent No.: US 9,207,518 B2
(45) Date of Patent: *Dec. 8, 2015

(54) 360° IMAGING SYSTEM

(71) Applicant: IMPLICITCARE, LLC, West Hollywood, CA (US)

(72) Inventors: Gregory Paul Mueller, West Hollywood, CA (US); Ted Gagliano, Beverly Hils, CA (US); Charles Kreuser, West Hollywood, CA (US); Kenneth D. Salter, Glendale, CA (US)

(73) Assignee: IMPLICITCARE, LLC, West Hollywood, CA (US)

( * ) Notice: Subject to any disclaimer, the term of this patent is extended or adjusted under 35 U.S.C. 154(b) by 272 days.

This patent is subject to a terminal disclaimer.

(21) Appl. No.: 13/779,543

(22) Filed: Feb. 27, 2013

(65) Prior Publication Data
US 2013/0222684 A1 Aug. 29, 2013

Related U.S. Application Data

(60) Provisional application No. 61/603,853, filed on Feb. 27, 2012, provisional application No. 61/667,108, filed on Jul. 2, 2012.

(51) Int. Cl.
*G03B 17/56* (2006.01)
*F16M 11/18* (2006.01)
(Continued)

(52) U.S. Cl.
CPC ............ *G03B 17/561* (2013.01); *A61B 5/0064* (2013.01); *A61B 5/0077* (2013.01); *A61B 5/1079* (2013.01); *A61B 5/6889* (2013.01); *F16M 11/046* (2013.01); *F16M 11/048* (2013.01); *F16M 11/18* (2013.01); *F16M11/2014* (2013.01); *F16M 11/2021* (2013.01); *F16M 11/28* (2013.01); *F16M 11/42* (2013.01); *F16M 13/02* (2013.01); *F16M 13/027* (2013.01); *G03B 15/06* (2013.01)

(58) Field of Classification Search
None
See application file for complete search history.

(56) References Cited

U.S. PATENT DOCUMENTS

| 706,459 A | 8/1902 | Selke |
| 2,140,602 A | 10/1937 | Simjian |

(Continued)

FOREIGN PATENT DOCUMENTS

| JP | 401092732 A | 4/1989 |
| JP | 2005038293 A | 2/2005 |
| JP | 2005316051 A | 11/2005 |

OTHER PUBLICATIONS

International Search Report and Written Opinion issued on May 9, 2013 in PCT/US2013/028092.

*Primary Examiner* — Kate Luo
(74) *Attorney, Agent, or Firm* — Jeffer Mangels Butler & Mitchell LLP; Brennan C. Swain, Esq.

(57) ABSTRACT

A 360 degree camera imaging system comprising a first horizontal boom having a first end, a second end, and a middle section; a second horizontal boom having a first end and a second end; a first vertical arm having a first end and a second end; a second vertical arm having a first end and a second end; and a mounting bracket. The first horizontal boom is connected to the first end of the second horizontal boom by a first rotatable pivot proximate the middle section of the first horizontal boom, and the second end of the second horizontal boom is connected to the mounting bracket. The first end of the first vertical arm is affixed to the first end of the first horizontal boom, and the first end of the second vertical arm is affixed to the second end of the first horizontal boom. A camera is mounted to the first vertical arm, and a backdrop is mounted to the second vertical arm.

15 Claims, 19 Drawing Sheets

(51) Int. Cl.
*G03B 15/06* (2006.01)
*A61B 5/00* (2006.01)
*A61B 5/107* (2006.01)
*F16M 11/04* (2006.01)
*F16M 11/20* (2006.01)
*F16M 11/28* (2006.01)
*F16M 11/42* (2006.01)
*F16M 13/02* (2006.01)

(56) References Cited

U.S. PATENT DOCUMENTS

| | | | |
|---|---|---|---|
| 2,448,084 A * | 8/1948 | Davis | 396/20 |
| 3,690,242 A | 9/1972 | Cruickshank | |
| 3,970,835 A | 7/1976 | Crete | |
| 4,236,795 A * | 12/1980 | Kephart | 396/5 |
| 4,302,097 A | 11/1981 | Chlestil | |
| 4,571,638 A | 2/1986 | Schneider | |
| 6,633,328 B1 | 10/2003 | Byrd | |
| 6,834,960 B2 | 12/2004 | Dbjay | |
| 7,039,220 B2 * | 5/2006 | Kriesel | 382/110 |
| 7,502,174 B2 * | 3/2009 | Jensen et al. | 359/694 |
| 7,720,554 B2 | 5/2010 | DiBernardino | |
| 2004/0037468 A1 | 2/2004 | Morishima | |
| 2006/0147188 A1 | 7/2006 | Weng | |
| 2007/0098378 A1 | 5/2007 | Giacomuzzi | |
| 2010/0232773 A1 | 9/2010 | DePaula | |
| 2011/0013197 A1 * | 1/2011 | Schwarz et al. | 356/601 |
| 2011/0116782 A1 | 5/2011 | Scott | |

* cited by examiner

360° IMAGING SYSTEM

CROSS REFERENCE TO RELATED APPLICATIONS

This application claims the benefit of U.S. Provisional Patent Application No. 61/603,853, filed on Feb. 27, 2012, and U.S. Provisional Patent Application No. 61/667,108, filed on Jul. 2, 2012, the entireties of which are incorporated herein by reference.

FIELD OF THE INVENTION

The present invention relates to a 360° imaging system, and more particularly to a 360° imaging system that can be used to image a patient prior to plastic surgery.

BACKGROUND OF THE INVENTION

In the field of plastic surgery, it is often desirable to document a patient's appearance before and after surgery. Photography is the usual means of documentation. However, often a photograph from one angle or even several angles is not sufficient to show the true transformation. Accordingly, a need exists for a system that documents up to a full 360° view of a patient before and after surgery.

SUMMARY OF THE PREFERRED EMBODIMENTS

The invention includes an articulated swiveling horizontal boom adapted to carry on one of its extremities a device, such as a video camera, still camera or other imaging device, which can be moved 360°. On the opposite end of the horizontal boom is mounted a backdrop that will rotate in synchrony about the vertical axis with the camera. The horizontal boom swivels about a vertical axis with the camera at one end and the background attached to the opposite end. The subject to be filmed is placed in a position that is generally co-axial with the vertical axis and is fixed in position. The camera travels 360° around the subject obtaining video imaging of the subject.

The "camera" end of the horizontal boom has a vertical arm or boom that extends downwardly and has the camera mounted thereon. The vertical arm or boom can be telescopic allowing lengthening or shortening to adjust the camera height. The "backdrop" end of the horizontal boom also includes a vertical arm or boom. This vertical arm or boom has the backdrop mounted thereon and travels opposite the video camera as the horizontal boom rotates. A lighting system is mounted on the "camera" end of the horizontal boom and on the vertical arm or boom that holds the imaging device. The lighting system provides downward lighting and front lighting of the subject that remains consistent as the camera rotates around the subject. A third light can be located toward the opposite end of the horizontal boom close to the vertical axis. This light source illuminates the background, thus preventing shadowing created from the two other light sources. All of these light fixtures are adjustable in location and intensity depending on the need to illustrate features of the object being imaged. Motorized movement control may be provided to rotate the imaging system and background around the subject, or to lower or raise each vertical arm or boom, or to articulate the vertical arms or booms upwards or downwards.

The imaging system can be oriented to capture images in either portrait or landscape orientation depending on the needs of the project. Preferably, when imaging the human body the camera is positioned to obtain portrait images that are vertically oriented.

Imaging of the human body, face, head and neck preferably includes the use of video imaging with a high-resolution system. In an exemplary embodiment, for the purposes of cosmetic surgery planning for the head and neck, the camera obtains two video clips of the subject with the first 360° scan being taken when the subject is in repose and the second 360° scan would be taken with the patient smiling. The subject can be seated on an adjustable stool allowing the raising and lowering of the subject to the appropriate level of the camera or through adjustment of the camera arm.

In a preferred embodiment, the imaging system includes an automated process for capturing, editing, storing, retrieving and compositing orbital shot footage. The system includes a motion controlled armature (or series of booms) which rotates the camera, lights and backdrop around the patient at a repeatable rate. The imaging device can be programmed (or manually moved) to stop at any position within the orbit, allowing the camera to pause at one or more points through the orbit. In a preferred embodiment, lighting can be programmed to change intensity, color temperature or source/direction. In an exemplary embodiment, the operator initializes the system using a touchscreen and enters patient metadata (e.g., name, surgical procedure, etc.). The patient is positioned, either seated or standing, under the axis of rotation, with the assistance of an eye safe laser (or other positioning device). In use, the operator reaches overhead and lowers the camera and backdrop into a fixed position for the scan. The camera elevation can be set over a wide range (e.g., 6" to 80") to scan any horizontal band of the patient's body.

In accordance with an aspect of the present invention there is provided a 360 degree camera imaging system comprising a first horizontal boom having a first end, a second end, and a middle section; a second horizontal boom having a first end and a second end; a first vertical arm having a first end and a second end; a second vertical arm having a first end and a second end; and a mounting bracket. The first horizontal boom is connected to the first end of the second horizontal boom by a first rotatable pivot proximate the middle section of the first horizontal boom, and the second end of the second horizontal boom is connected to the mounting bracket. The first end of the first vertical arm is affixed to the first end of the first horizontal boom, and the first end of the second vertical arm is affixed to the second end of the first horizontal boom. A camera is mounted to the first vertical arm, and a backdrop is mounted to the second vertical arm. In a preferred embodiment, the second end of the second horizontal boom is connected to the mounting bracket by a second rotatable pivot. Preferably, the backdrop is mounted to the second vertical arm by way of a third rotatable pivot. Preferably, a light is mounted on the first vertical arm. Preferably, a second light mounted on the second vertical arm, proximate the first end of the second vertical arm. Preferably, the camera is a video camera. Preferably the 360 degree camera imaging system further comprises a second camera. Preferably, the second camera is a still camera. Preferably, an electric motor is affixed to the second horizontal boom. Preferably, the electric motor is affixed proximate the first rotatable pivot. Preferably, the 360 degree camera imaging system further comprises a color scale. Preferably, the 360 degree camera imaging system further comprises a light emitting diode centering light.

In accordance with another aspect of the present invention there is provided a 360 degree camera imaging system comprising a horizontal boom having a first end, a second end, and a middle section; a first vertical arm having a first end and a second end; a second vertical arm having a first end and a second end; and a rotatable pivot proximate the middle section of the horizontal boom. The first end of the first vertical arm is affixed to the first end of the first horizontal boom, and the first end of the second vertical arm is affixed to the second end of the first horizontal boom. A camera is mounted to the first vertical arm, and a backdrop is mounted to the second vertical arm.

In accordance with another aspect of the present invention there is provided a method of using a 360 degree camera system to capture a set of before and after images of a subject, the method comprising the steps of (1) positioning the subject in between a camera and a backdrop at a first position, (2) passing the camera in a generally circular path around the subject while using the camera to capture at least five images of at least a portion of the subject, so as to capture a first image set, (3) positioning the subject a second time in between the camera and the backdrop at approximately the first position, (4) passing the camera in a generally circular path around the subject while using the camera to capture at least five images of at least a portion of the subject, so as to capture a second image set, and (5) comparing the first image set to the second image set. In a preferred embodiment, the method further comprises the use of a second camera that is a still camera, which captures at least five images while the first image set is being captured and at least five images while the second image set is being captured. Preferably, the first light is located generally in front of the subject, and a second light is located generally behind the subject. In a preferred embodiment, the rate of camera movement during capture of the first image set as compared to camera movement during capture of the second image set is substantially the same. Preferably, a subset of images from the first image set are selected. Preferably, a subset of images from the second image set are selected. In a preferred embodiment, the camera passes through at least about 360 degrees while capturing the first image set and through at least about 360 degrees while capturing the second image set. Preferably, a first side-by-side image of the subject and at least a second side-by-side image of the subject are produced. Preferably, the first side-by-side image of the subject includes an image from the first image set and an image from the second image set, and the second side-by-side image of the subject includes an image from the first image set and an image from the second image set.

The invention, together with additional features and advantages thereof may be best understood by reference to the following description.

DETAILED DESCRIPTION OF THE PREFERRED EMBODIMENTS

Figure 1:
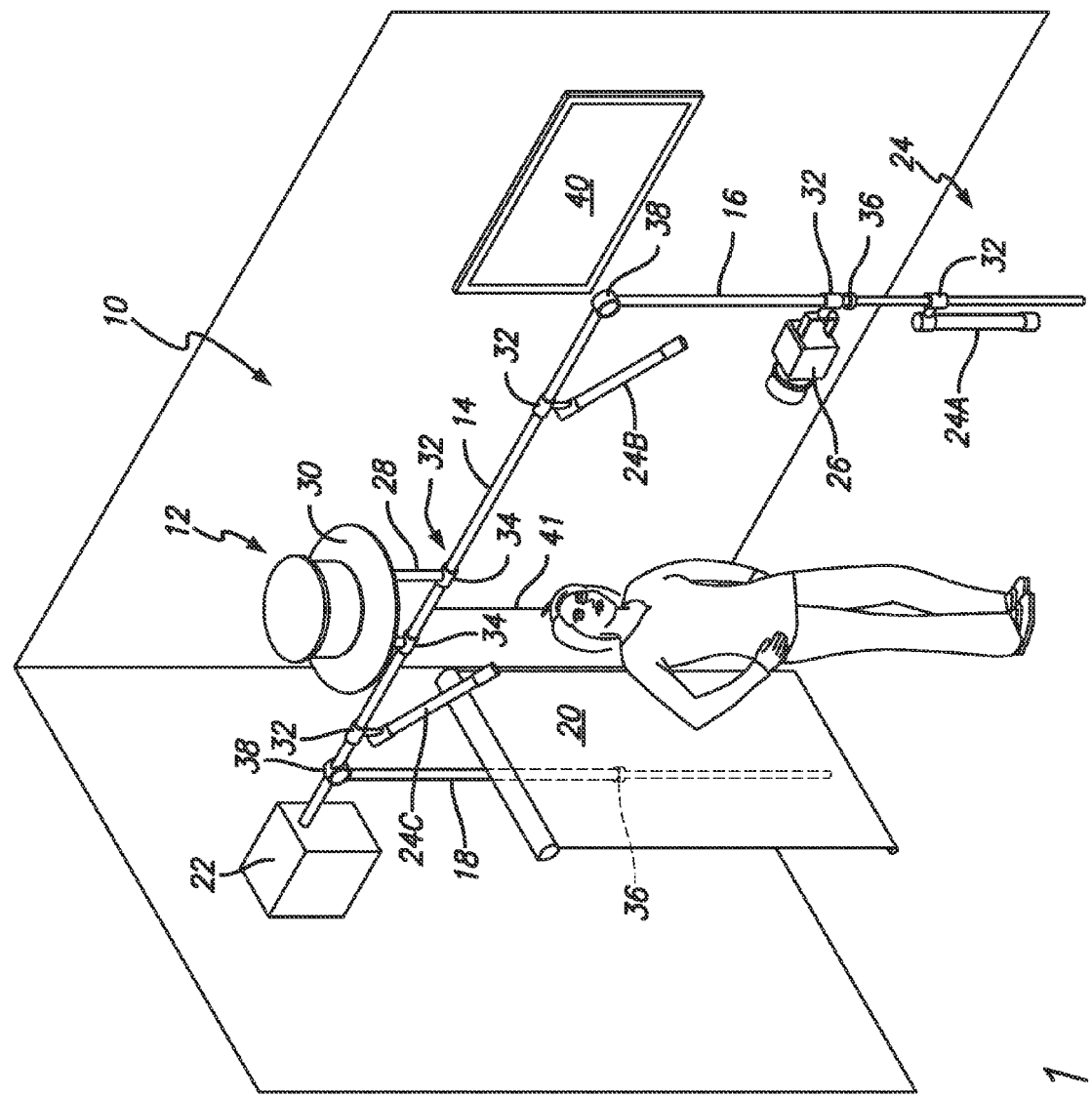
FIG. 1 is a perspective view of a 360° imaging system in accordance with a preferred embodiment of the present invention.

The following description and drawings are illustrative and are not to be construed as limiting. Numerous specific details are described to provide a thorough understanding of the disclosure. However, in certain instances, well-known or conventional details are not described in order to avoid obscuring the description. References to one or an embodiment in the present disclosure can be, but not necessarily are references to the same embodiment; and, such references mean at least one of the embodiments.

Reference in this specification to "one embodiment" or "an embodiment" means that a particular feature, structure, or characteristic described in connection with the embodiment is included in at least one embodiment of the disclosure. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments.

The terms used in this specification generally have their ordinary meanings in the art, within the context of the disclosure, and in the specific context where each term is used. Certain terms that are used to describe the disclosure are discussed below, or elsewhere in the specification, to provide additional guidance to the practitioner regarding the description of the disclosure. For convenience, certain terms may be highlighted, for example using italics and/or quotation marks: The use of highlighting has no influence on the scope and meaning of a term; the scope and meaning of a term is the same, in the same context, whether or not it is highlighted. It will be appreciated that the same thing can be said in more than one way.

Consequently, alternative language and synonyms may be used for any one or more of the terms discussed herein. Nor is any special significance to be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only, and is not intended to further limit the scope and meaning of the disclosure or of any exemplified term. Likewise, the disclosure is not limited to various embodiments given in this specification.

Without intent to further limit the scope of the disclosure, examples of instruments, apparatus, methods and their related results according to the embodiments of the present disclosure are given below. Note that titles or subtitles may be used in the examples for convenience of a reader, which in no way should limit the scope of the disclosure. Unless otherwise defined, all technical and scientific terms used herein have the same meaning as commonly understood by one of ordinary skill in the art to which this disclosure pertains. In the case of conflict, the present document, including definitions, will control.

It will be appreciated that terms such as "front," "back," "upper," "lower," "side," "short," "long," "up," "down," and "below" used herein are merely for ease of description and refer to the orientation of the components as shown in the figures. It should be understood that any orientation of the components described herein is within the scope of the present invention.

Referring now to the drawings, which are for purposes of illustrating the present invention and not for purposes of limiting the same, FIG. 1 shows a preferred embodiment of a 360° imaging system 10 in accordance with a preferred embodiment of the present invention. The imaging system 10 can be used to take 360° pictures or videos of a person, object or scene positioned about a substantially vertical axis. The system 10 is preferably suspended from the ceiling and includes an imaging device that is pointed toward the object and is rotatable about the substantially vertical axis. In the exemplary embodiment described herein, the system 10 is used for imaging plastic surgery patients (e.g., to show before and after results). However, this is not a limitation on the present invention and it will be understood that the system 10 can be used for imaging any desired object.

Figure 2:
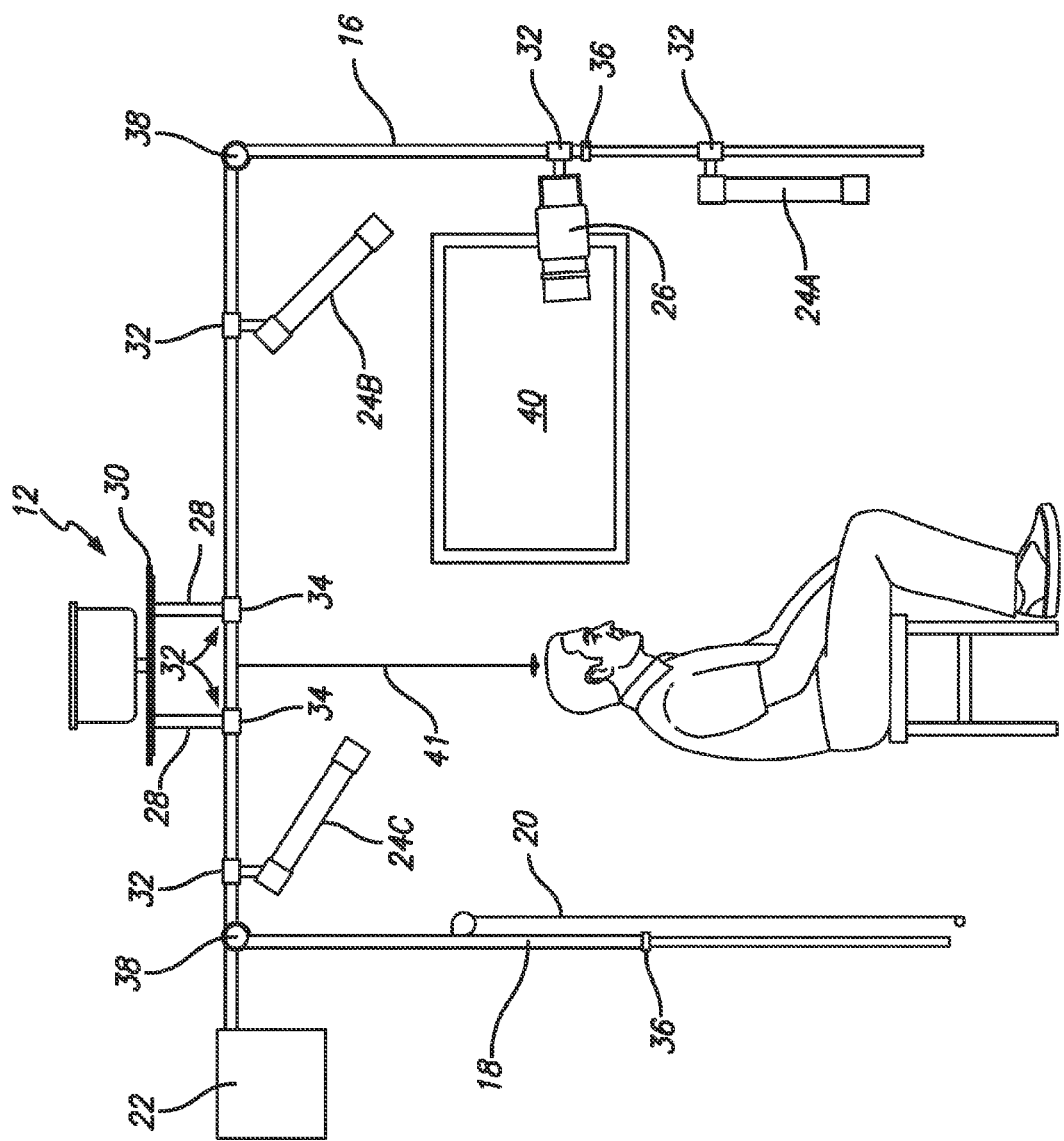
FIG. 2 is a side elevational view of the 360° imaging system of FIG. 1.
Figure 3:
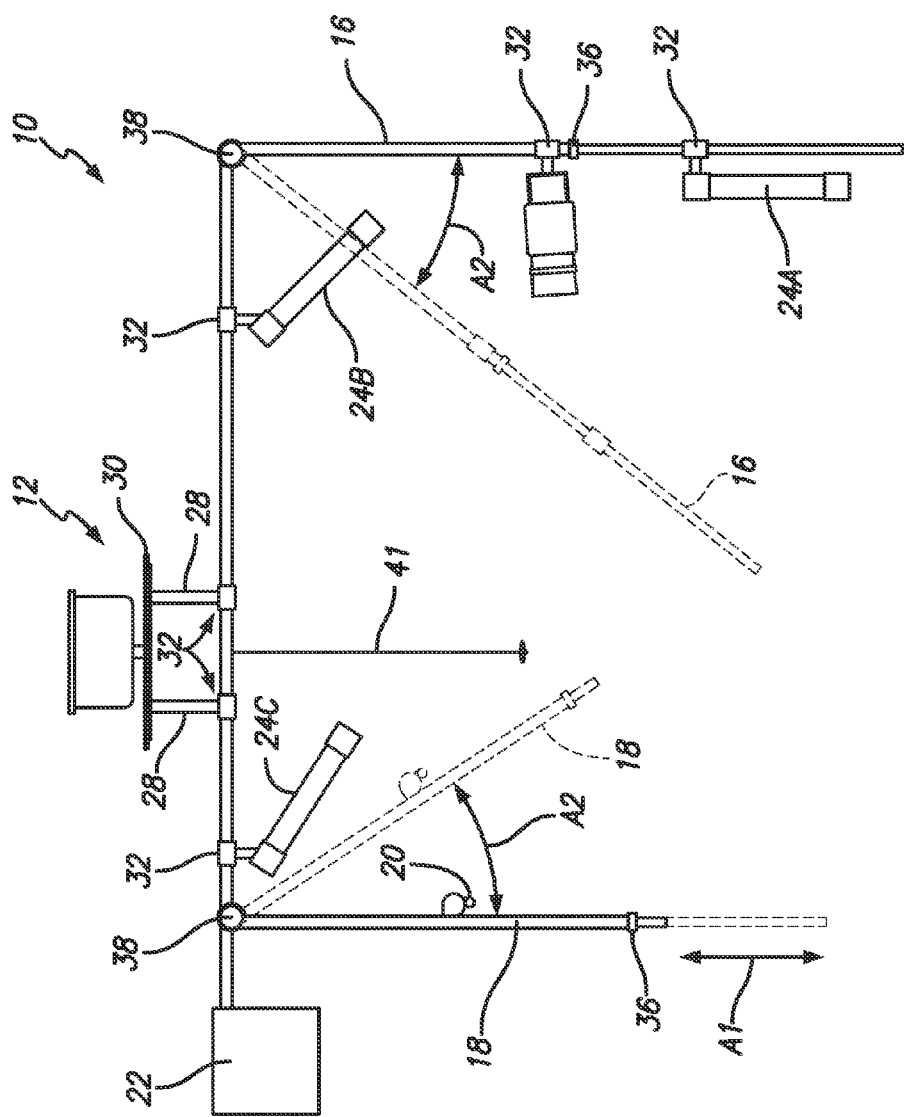
FIG. 3 is a side elevational view of the 360° imaging system of FIG. 1 showing the pivotal adjustability of the horizontal arms.

As is shown in FIGS. 1-3, in a preferred embodiment, the imaging system 10 includes a rotation device 12 having a horizontally oriented boom 14 depending therefrom, first and second vertically oriented booms or arms 16 and 18, a backdrop 20, a counterweight 22, a lighting system 24 and an image capture device 26. In a preferred embodiment, the rotation device 12 is attached to or built into the ceiling of a room and includes a shaft or shafts 28 extending downwardly therefrom. As is best shown in FIG. 2, in a preferred embodiment, the rotation device 12 includes a rotatable plate 30 to which the shafts 28 are attached. The opposite ends of the shafts are associated with the horizontal boom 14. The shafts 28 can be attached directly to the horizontal boom 14 or the shafts can include a slidable adjustment member 32 through which the horizontal boom 14 extends. It will be appreciated by those skilled in the art that any type of adjustment member that allows the horizontal boom 14 to be adjusted in a horizontal or axial direction is within the scope of the present invention. For example, the slidable adjustment member 32 can be a tube 34 through which the horizontal boom 14 extends and that includes a set screw (not shown) that holds the horizontal boom 14 in place.

As shown in FIGS. 2-3, in a preferred embodiment, first and second vertical arms 16 and 18 extend downwardly from horizontal boom 14. First vertical arm 16 includes image capture device 26 secured thereon. In a preferred embodiment, the height of image capture device 26 is adjustable. This can be done via a slidable adjustment member 32, as described above or by another known method. In another embodiment, the first vertical arm 16 itself can be adjustable, for example by a telescopic adjustment member 36 or by providing for movement vertically of the entire first vertical arm 16. In a preferred embodiment, second vertical arm 18 includes backdrop 20 secured thereon. The height of backdrop 20 or second vertical arm 18 can also be adjustable. See, e.g., telescopic adjustment member 36 and arrow A1 in FIG. 3. Furthermore, backdrop 20 can be raised or lowered, as is known in the art. In a preferred embodiment, the first and second vertical arms 18 and 20 are also pivotally adjustable as shown by arrows A2 in FIG. 3. As will be appreciated by those skilled in the art, pivotal adjustment can be provided by pivotal adjustment members 38 or the like.

As is shown in FIGS. 1-3, lighting system 24 includes a plurality of lights 24a, 24b and 24c. Any number of lights is within the scope of the present invention, and will depend on the needs of the particular project. In an exemplary embodiment, the light system 24 includes a first light 24a disposed on first vertical arm 16 for front lighting of the subject, a second light 24b for downward front lighting and a third light 24c for lighting the backdrop 20. In a preferred embodiment each of the lights 24 are adjustable, such as by a slidable adjustment member 32, as described above. In another embodiment, the lights 24 can be clipped onto the horizontal boom 14 or first and/or second vertical arms 16 and 18.

In a preferred embodiment, horizontal boom 14 includes counterweight 22 at or near the end thereof that is opposite the end that includes the image capture device 26. Counterweight 22 helps balance the system. The counterweight 22 can also be adjustable or movable to account for the weight of image capture device 26, lights 24, backdrop 20 and other components. Wires for carrying electricity, video signals, etc. are not shown in the drawings. However, those of ordinary skill in the art will understand the need for wires or conductors, etc. for powering the image capture device 26, lights 24, etc. It is also within the scope of the invention that the video and/or audio signals be sent wirelessly.

As shown in FIG. 1, in a preferred embodiment, the system 10 includes a monitor that displays the image being captured by the image capture device 26. The monitor 40 can also be used to play back the captured image(s). The image capture device 26 and monitor are in electrical communication via wires or wirelessly.

As shown in FIGS. 1-3, in a preferred embodiment, the imaging system 10 includes a plumb line 41 that extends downwardly from the horizontal boom 14 or the rotation device 12 and that is positioned substantially co-axially with the vertical axis defined by the rotation of the horizontal boom 14. In another embodiment, the plumb line can be omitted. In use, the subject to be filmed is placed in a position that is generally co-axial with the plumb line 41 and the vertical axis and is fixed in position. As shown in FIGS. 1 and 2, the subject can be seated or standing, as desired. The horizontal boom 14 is then rotated about the vertical axis with the image capture device 26 at one end and the background 20 attached to the opposite end. Preferably, the image capture device 26 travels 360° around the subject obtaining video imaging of the subject. In this configuration, the subject is always positioned between the image capture device 26 and the back drop 20. The counterweight 22 is positioned such that it helps maintain balance of the system so that the image capturing device 26 moves in a 360° are in as close to a perfect circle as possible. In other words, the counterweight 22 helps prevent the image capturing device from moving up and down or swinging left to right, as it moves in a circle and captures the desired image.

Figure 4:
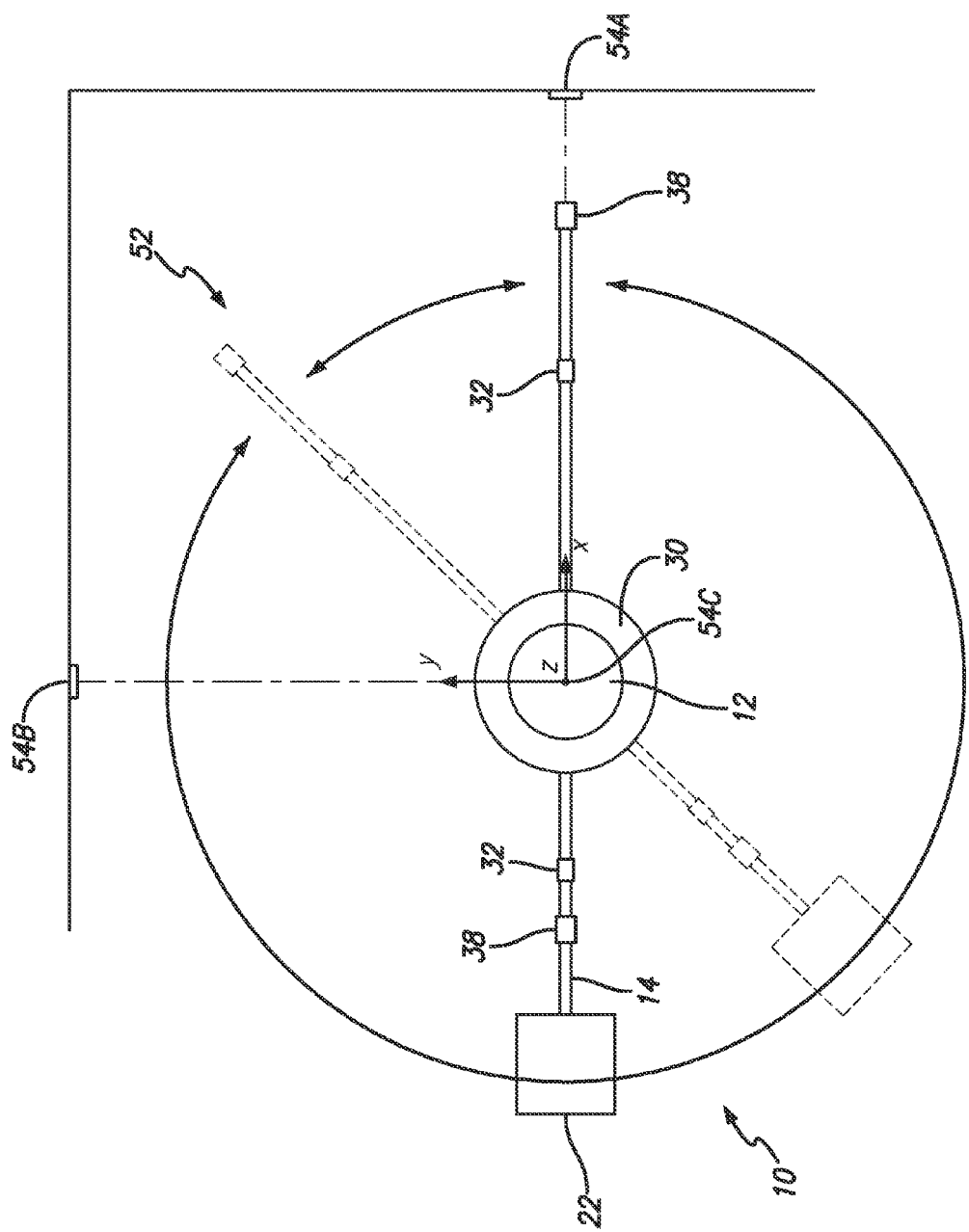
FIG. 4 is top plan view of the imaging system of FIG. 1 together with a centering system in accordance with an embodiment of the invention.
Figure 5:
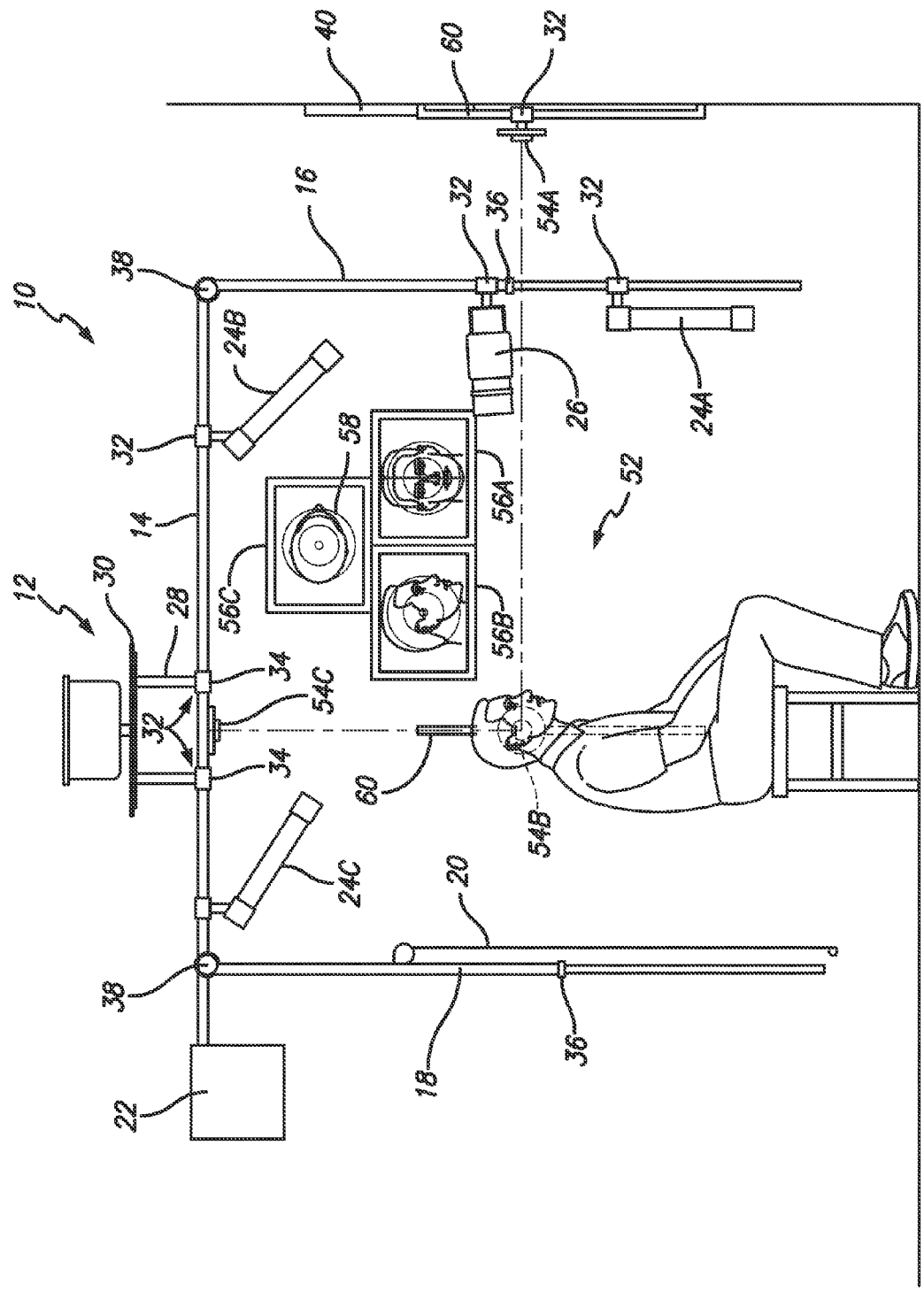
FIG. 5 is a side elevational view of the 360° imaging system of FIG. 1 together with the centering system of FIG. 4.

FIGS. 4-5 shows the imaging system 10 together with a centering system 52. In a preferred embodiment, centering system 52 includes three cameras or image capturing devices 54a, 54b and 54c positioned such that they are directed toward the point where the object to be imaged is optimally centered. These cameras are positioned to capture the front view (x-axis camera 54a), side or lateral view (y-axis camera 54b) and top view (z-axis camera 54c). In a preferred embodiment, the images from these cameras 54a-54c are communicated to one or more monitors 56a, 56b and 56c where the user of the system 52 can position the object to be filmed as desired. It will be understood that the images can be positioned on a single monitor or on separate monitors. In another embodiment, the images can be shown on monitor 40.

In a preferred embodiment, the three monitors 56a-56c are positioned on the wall and each include circles or markers 58 thereon that represent the optimal centered position. In use, using an example where the patient's head is being imaged, after the patient is seated, the surgeon can tell the patient to move their head, left, right, back, forth, etc. until their head is positioned as desired by the surgeon. This arrangement helps with repeatability between the before and after images.

In a preferred embodiment, cameras 54a-54c are movable. For example, x-axis camera 54a and y-axis camera 54b can be moved vertically depending on what portion of a patient is to be imaged. As shown in FIG. 5, the x-axis camera 54a and y-axis camera 54b can be mounted on an arm 60 and include a slidable adjustment member 32. It should be understood that the x-axis camera 54a and y-axis camera 54b are usually positioned at the same height vertically. Therefore, in use, the z-axis camera 54c aids in positioning the patient along the center axis, and the x-axis camera 54a and y-axis camera 54b aid the user in finding the desired horizontal level to be imaged. It will be appreciated by those skilled in the art that cameras 54a-54b are independent of camera 26 and are preferably only used to center the patient. Camera 26 is used to image the patient as desired. The type of centering system used is not a limitation on the present invention.

Figure 6:
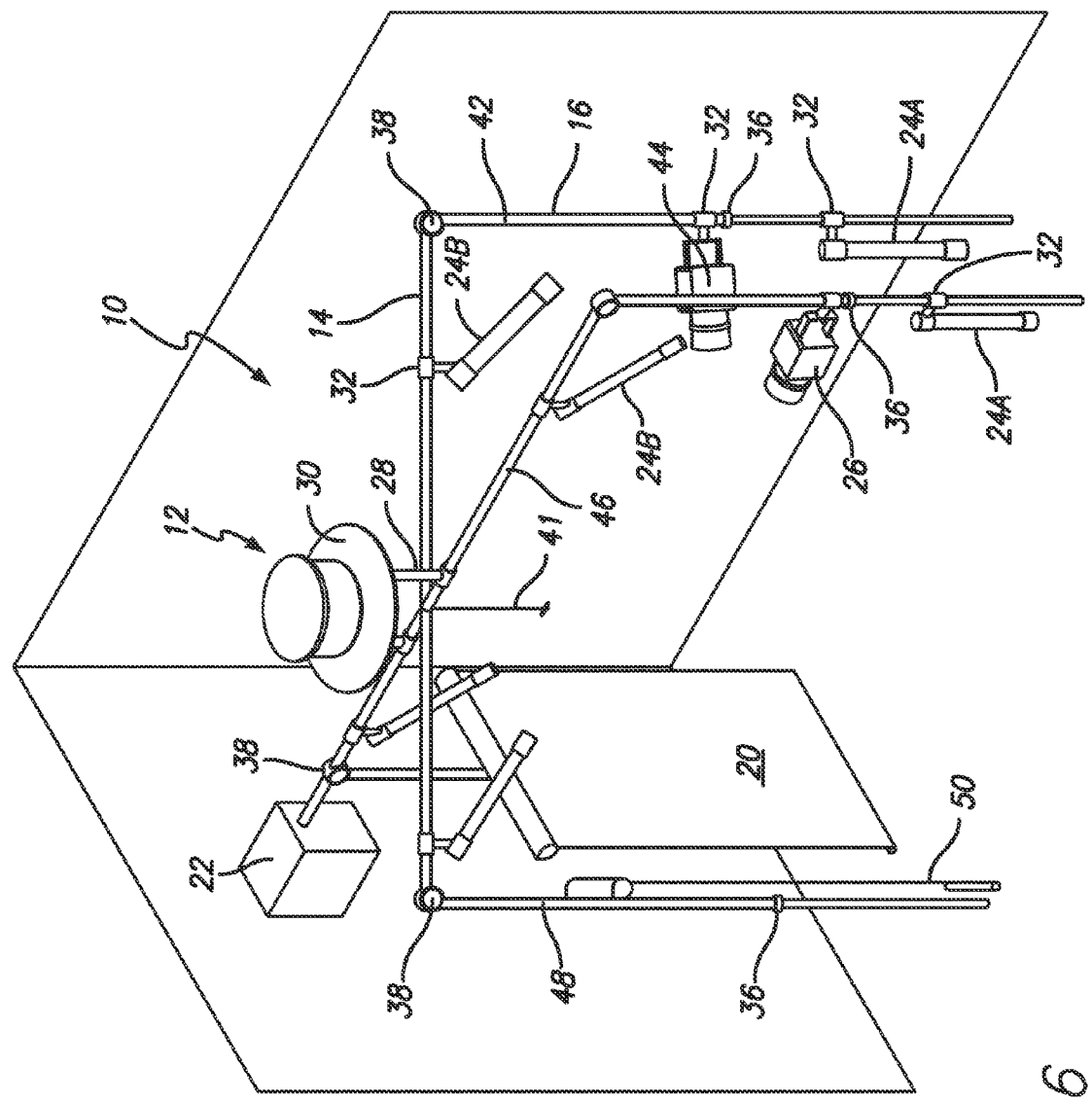
FIG. 6 is a perspective view of a 360° imaging system in accordance with another preferred embodiment of the present invention.

It will be understood that the system 10 can include multiple image capture devices 26. In one embodiment, the system 10 can include multiple image capture devices 26 on the first vertical arm 16, thereby allowing a larger vertical image capture area. In another embodiment, as shown in FIG. 6, the system 10 can include a third vertical arm 42 that includes a second image capture device 44. As shown in FIG. 6, in this embodiment, the system 10 can include a second horizontal boom 46, fourth vertical arm 48 and second backdrop 50. Any number of image capture devices, backdrops and associated booms or arms is within the scope of the present invention.

When used in the plastic surgery system the system 10 can be used for preoperative evaluation of the face, the body or extremities to assess the aging process or deformity. In an exemplary use, as shown in FIG. 2, the patient is seated as desired along the center axis, either by using the plumb line 41, centering system 52 or other centering methodology. The image capturing device 26 is then rotated 360° about the patient and the images are taken. In a preferred embodiment, the image capturing device 26 is rotated by hand. In other words, the user pushes or pulls the image capturing device 26 via the horizontal boom 14, first vertical arm 16 or other part of the system in a controlled manner around the patient. For example, the user focuses the camera 26, sets the desired exposure and then pushes the horizontal boom 14 and, because the system is counterbalanced via weight 22, it travels around the patient. In other embodiments, the rotation device 12 can be motorized and controlled remotely, by a switch, by computer or the like.

In a preferred embodiment, the image capture device 26 is a video camera. In an exemplary embodiment, the camera is a SONY® blu ray quality video camera that captures at least thirty frames per second as it passes around the patient. With this set up, the user can take any frame desired to make a photograph that can be used in patient evaluation, before and after pictures, etc.

The system 10 can be used so that the before and after images are standardized or taken under exactly the same conditions. In a preferred embodiment, the before and after images are taken using the same system 10, in the same location, with the patient positioned along the center axis, with approximately the same focal length from the patient and in a relatively dark room. Therefore, because the lighting system 24 travels with the image capturing device 26 the before and after images are relatively consistent. In an exemplary embodiment, after image capture pre and post-op, the user now has before and after dynamic three dimensional images and can also choose to select specific two dimensional images (or pictures) as desired.

Furthermore, as will appreciated by those skilled in the art, in plastic surgery the standard set of pictures of a patient is six different views. By using an image capture device 26 that captures thirty frames per second, even if the patient blinks or twitches or the like, with all of the separate images, a user will be able to find six separate images from the before and after image capturing sessions that help make an adequate comparison. This can be useful for showing to the patients, for marketing purposes or for a publication or paper authored by the plastic surgeon.

Continuing with an exemplary use in plastic surgery, the captured images can be used for patient evaluation both before and after surgery. For example, the images can be used with a prospective patient to point out areas that could use some work. In this scenario, after an image is taken, the plastic surgeon sits down with the patient and reviews the video clip rotating the patient's head, chest, abdomen or other body part in space, evaluating fat content, skin laxity, wrinkles. In an exemplary post-procedure use, for example after facial fat injections, the surgeon can look at the before and after head images next to each other and rotate them and look at an oblique view of the cheek to see if the results are satisfactory of if more fat needs to be injected.

The system 10 can also be used in the operating room when the patient is under general anesthesia so that the captured image(s) are free of blinking, movement, etc. The system 10 can also be used in the assessing of motor nerve function and facial nerve function and/or nerve function anywhere on the body by using the dynamic three-dimensional image.

In another embodiment of the invention, the imaging system 10 can be used in conjunction with placing the 3D markers on the skin or adjacent thereto. 3D markers for motion capture and the like are known. Accordingly, a description thereof will be omitted.

Figure 7:
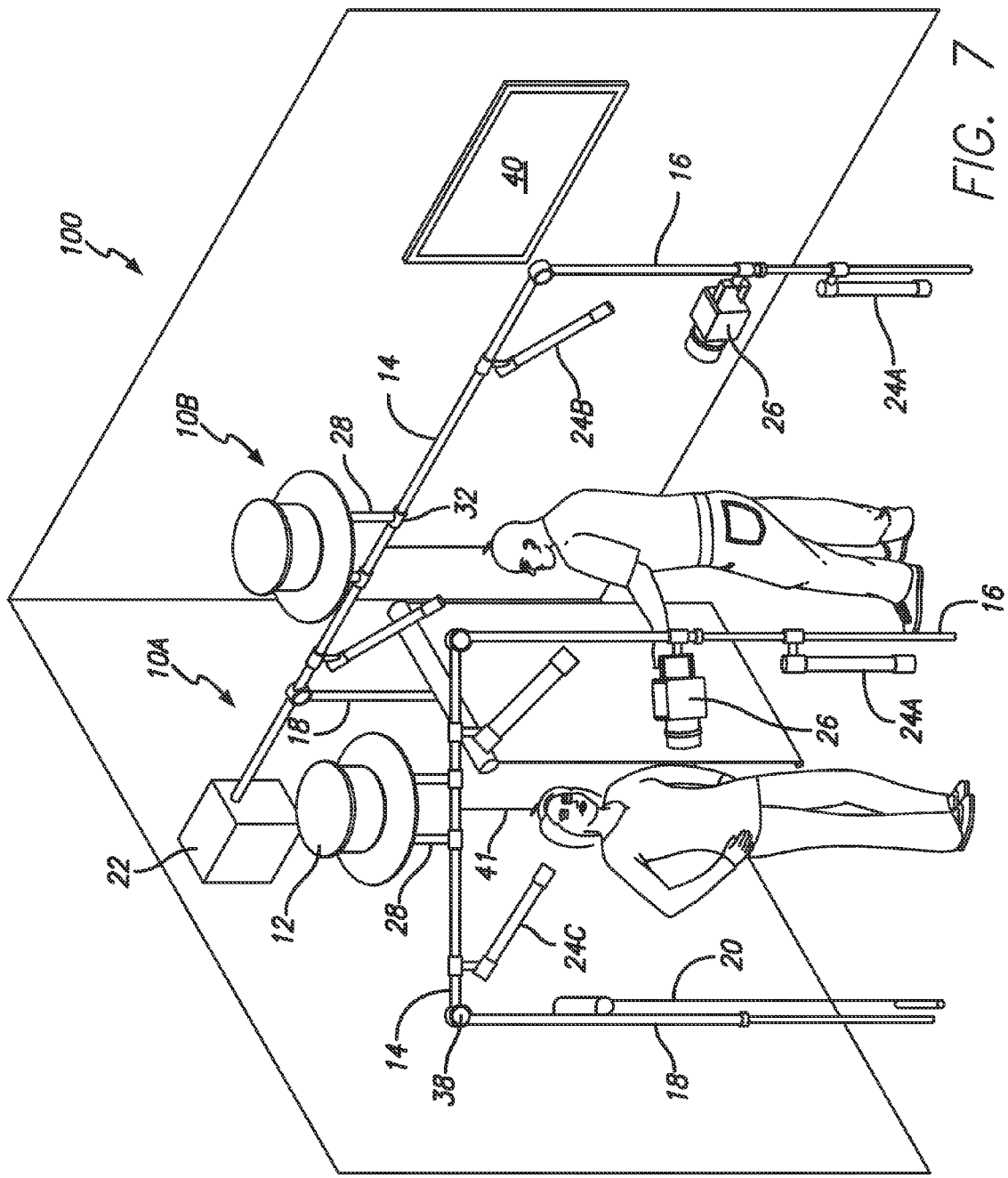
FIG. 7 is a perspective view of a dual 360° imaging system in accordance with another preferred embodiment of the present invention.
Figure 8:
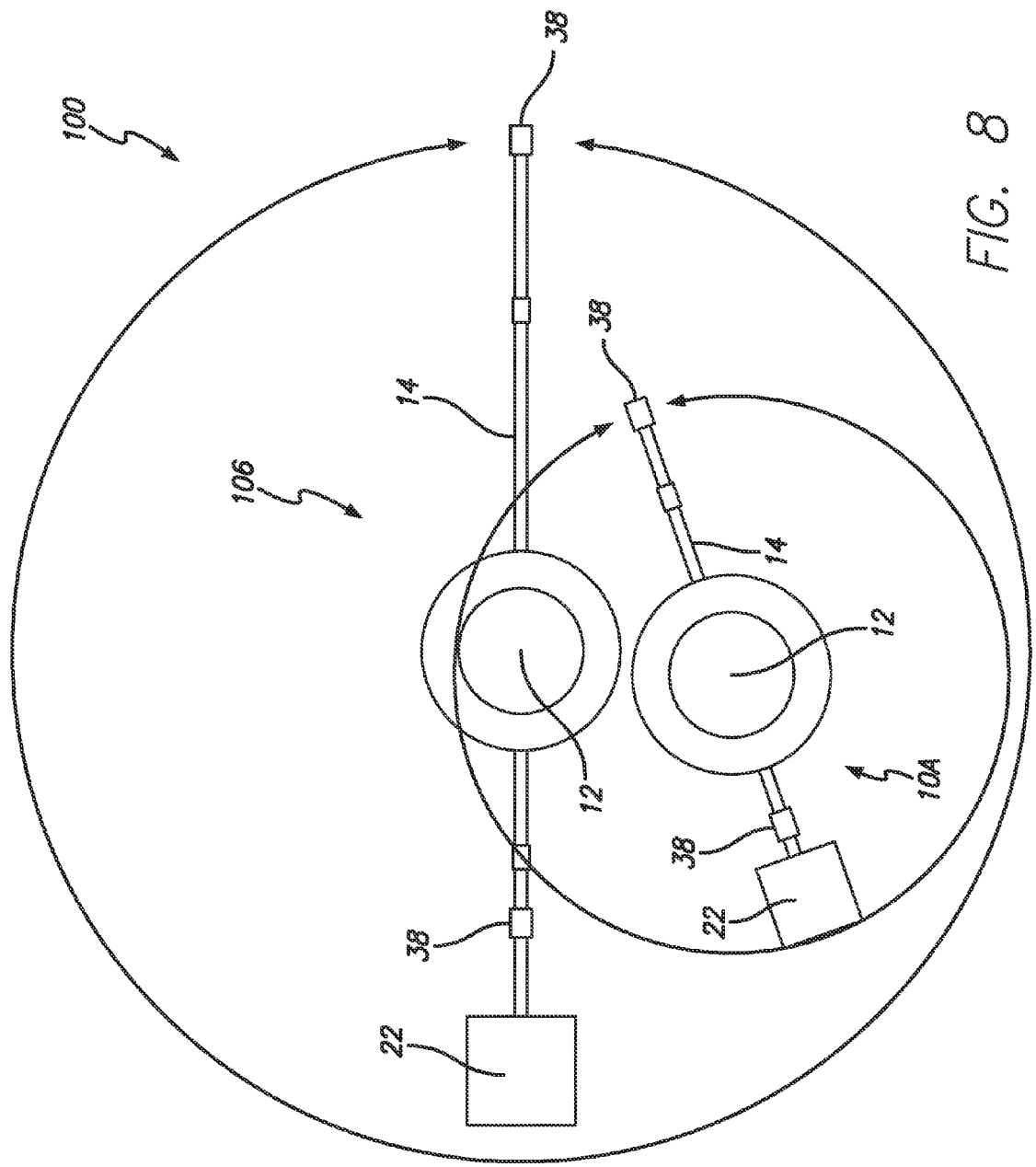
FIG. 8 is a top plan view of the dual 360° imaging system of FIG. 7.

FIGS. 7-8 show another embodiment of a 360° imaging system 200 that includes two systems 10a and 10b as described above, that operate in conjunction with one another. In a preferred embodiment, this system 100 can be used to film two subjects that are each positioned under the rotation device 12 and co-axial with the substantially vertical axis defined by the rotation device 12. As shown in the figures, in a preferred embodiment, one system 10a has a shorter horizontal boom 14 than the other system 10b. This allows the booms 14 to rotate without components hitting one another. However, this is not a limitation on the present invention. As shown in FIG. 8, in a preferred embodiment, the systems 10a and 10b are positioned so that the first system 10a can rotate within the second system 10b.

Figure 9:
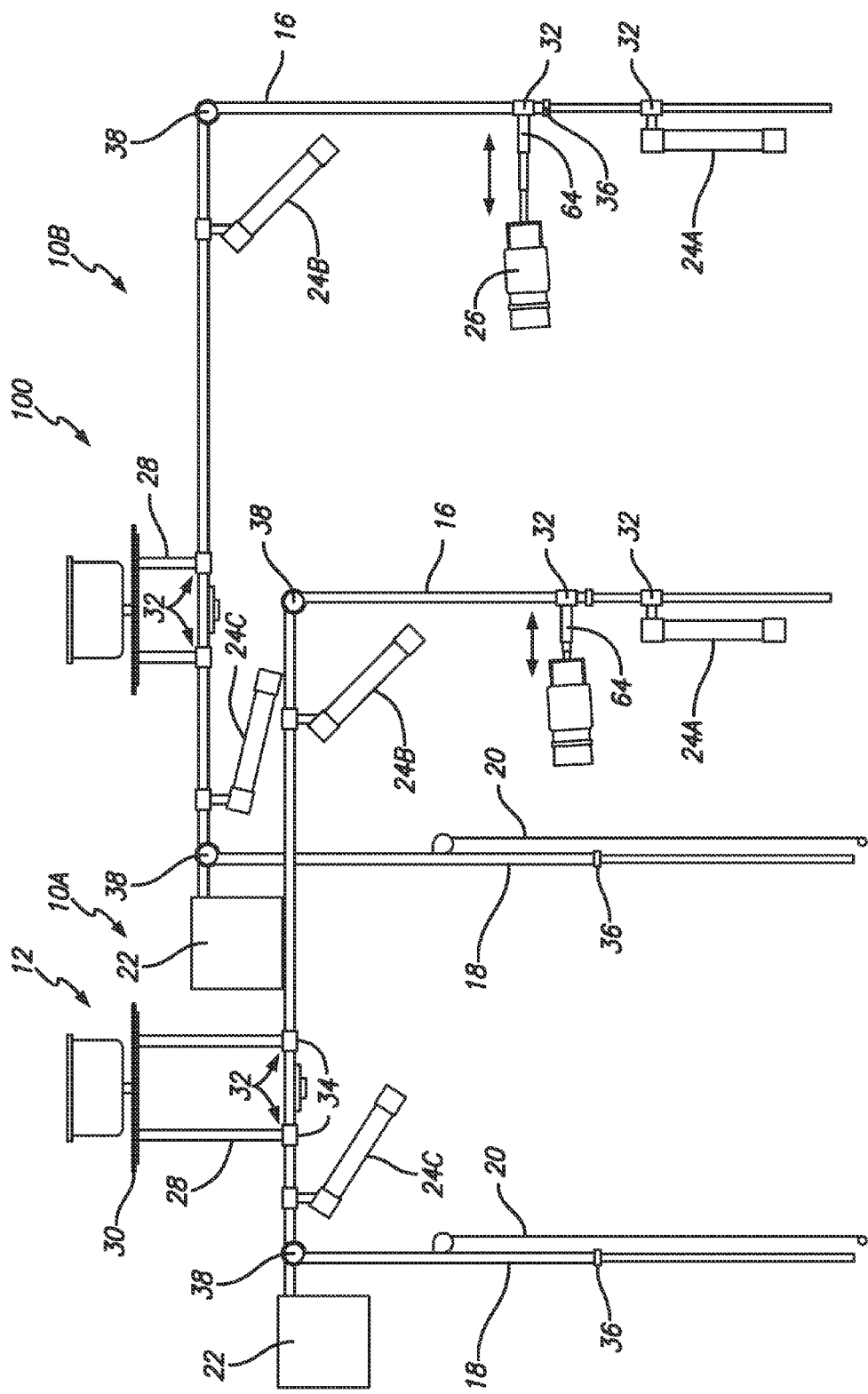
FIG. 9 is a side elevational view of the dual 360° imaging system of FIG. 7 with the camera mounted on a telescoping arm.

Also, in a preferred embodiment, the horizontal booms 14 are positioned at different heights to also allow movement without components hitting one another. This can be done by positioning the rotation devices 12 at different heights or providing different length shafts 28 and positioning the systems 10a and 10b as shown in FIG. 9. In a preferred embodiment, the system includes an arm 64 on which camera 26 is mounted and that moves horizontally (via telescoping or the like—see the arrows in FIG. 9) for close-ups and the like.

In an exemplary embodiment, the dual 360° imaging system 100 can be used in the film industry. For example, it can be used as a method for pre-visualization. It can be used to shoot scenes quickly with two actors who are each positioned under one of the rotation devices 12 and recite their lines. After shooting the scene and rotating each of the cameras 26 as desired, together with the backdrop 20 (which can be a blue screen or the like), the user has different angles to choose from without having to re-rig the camera, as has been done in the past. In this exemplary use, for pre-visualizing shoots, the dual 360° imaging system 100 allows a user to keep running a scene and have a plurality of different angles to choose from afterwards. And, the blue screen backdrop 20 stays lit behind the subject and the subject stays evenly lit because little changes between the camera 26 and the subject.

In an exemplary use, the subjects are each positioned on stools (or they can be standing) underneath the rotation devices of each of the systems. Then the cameras can separately be rotated around the two subjects as desired.

In another embodiment, the system can include the ability to move the camera in or out, i.e., in a horizontal direction. This can be done on an arm that moves horizontally, similar to the arms moving vertically described above. Or, the system can include a telescoping member on which the camera is mounted and that moves the camera toward and away from the subject. In a preferred embodiment, the movement of the system (rotation, up and down or in and out of cameras or arms) is automated. Therefore, in an exemplary use, a camera can move around the subject and then push in for a close up or pull back as desired. In a preferred embodiment, this can be done automatically at the sound of the director's voice.

Figure 10:
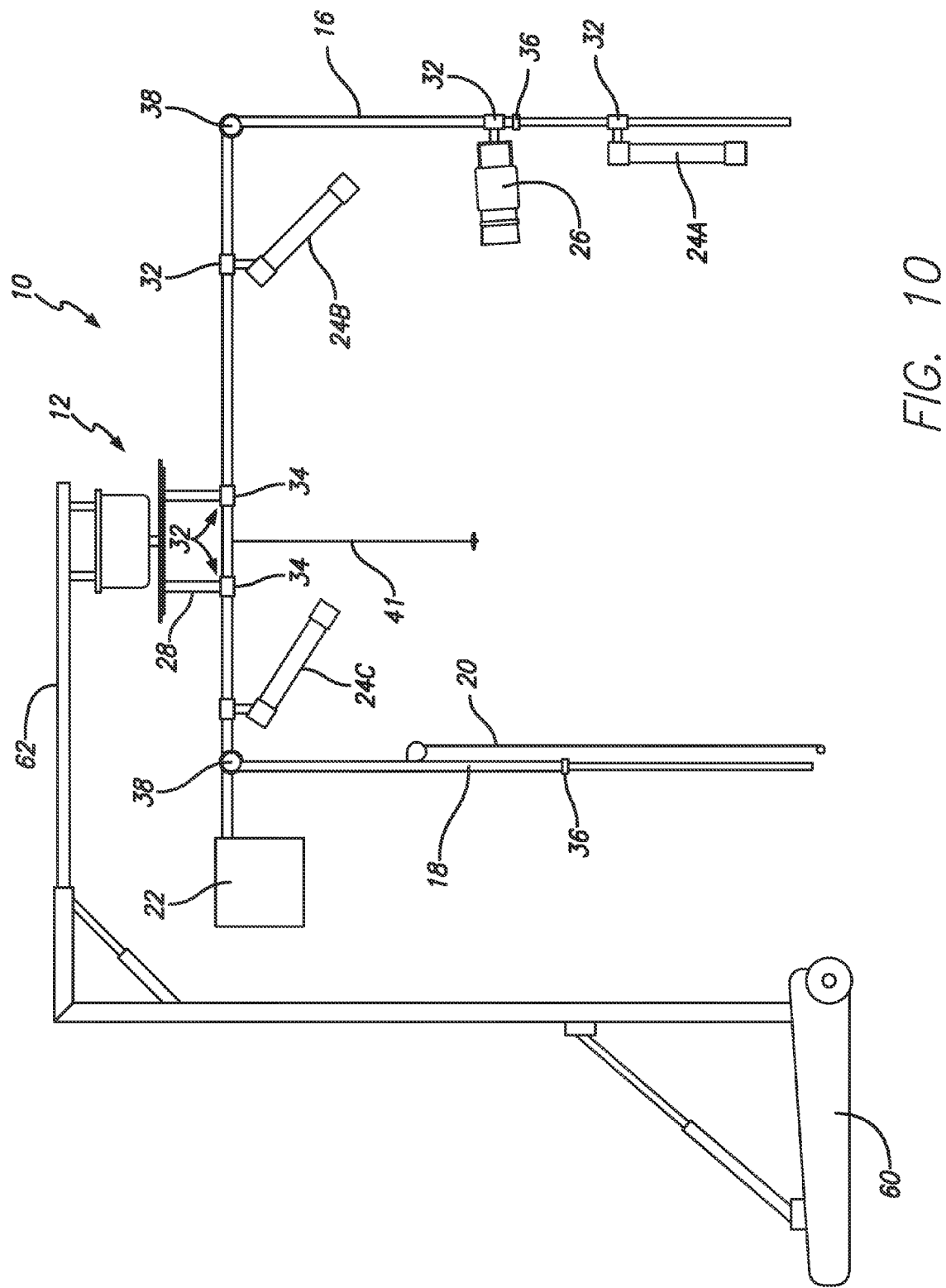
FIG. 10 is a side elevational view of a portable 360° imaging system in accordance with another preferred embodiment of the present invention.

As shown in FIG. 10, in another embodiment, the imaging system 10 can be portable. In a preferred embodiment, the system 10 includes a stand 60 or the like that includes an arm 62 that suspends the system 10 above the ground. In an exemplary embodiment, the stand 60 can be configured to be weighted down by being filled with water, sand or other material, similar to outdoor portable basketball systems. In yet another embodiment, the system can be positioned on a dolly or track so that the entire system can be moved horizontally and still be rotatable.

Figure 11A:
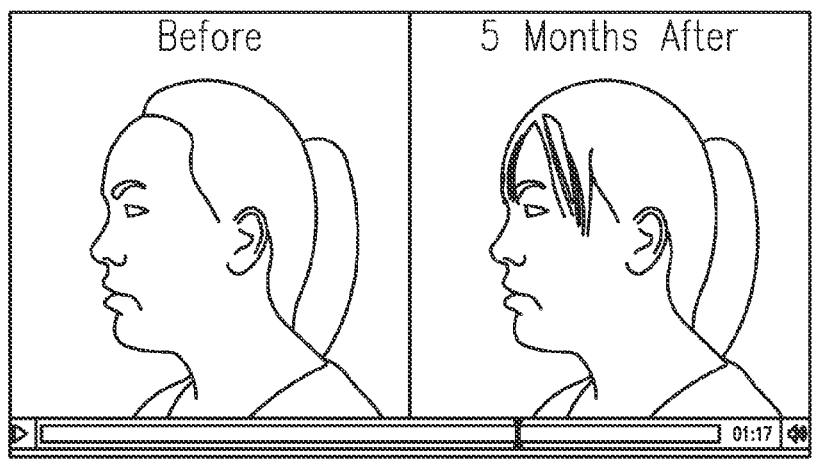
FIGS. 11A-11C are a series of images showing dual rotating before and after images in accordance with an embodiment of the present invention.
Figure 11B:
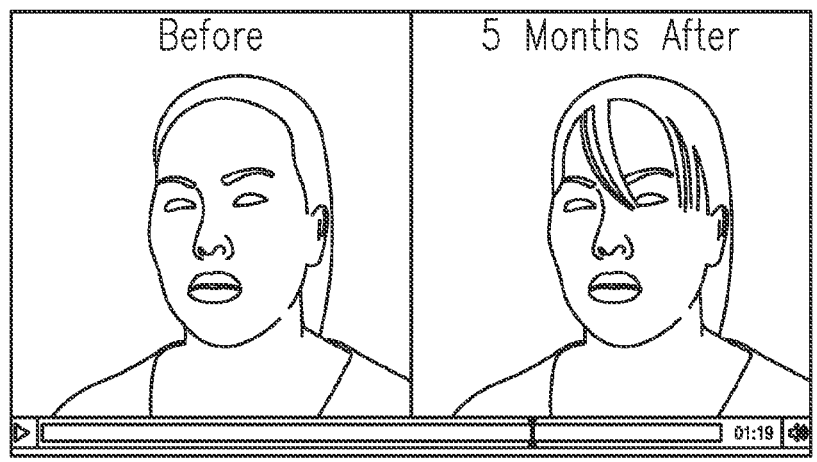
Figure 11C:
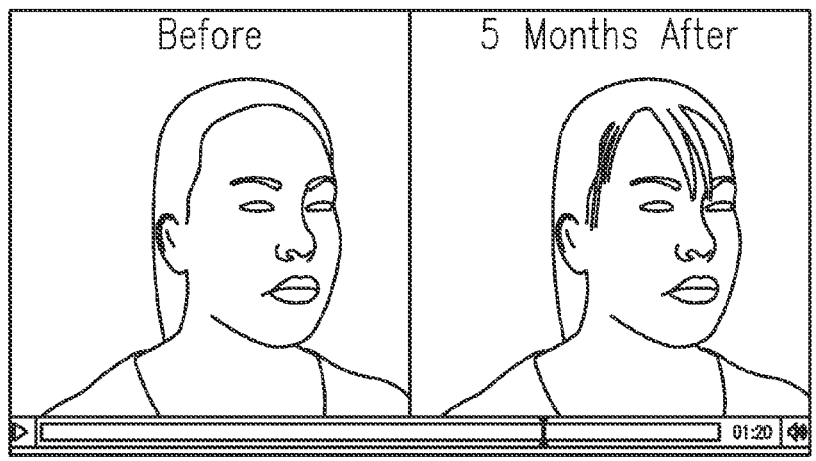
Figure 12:
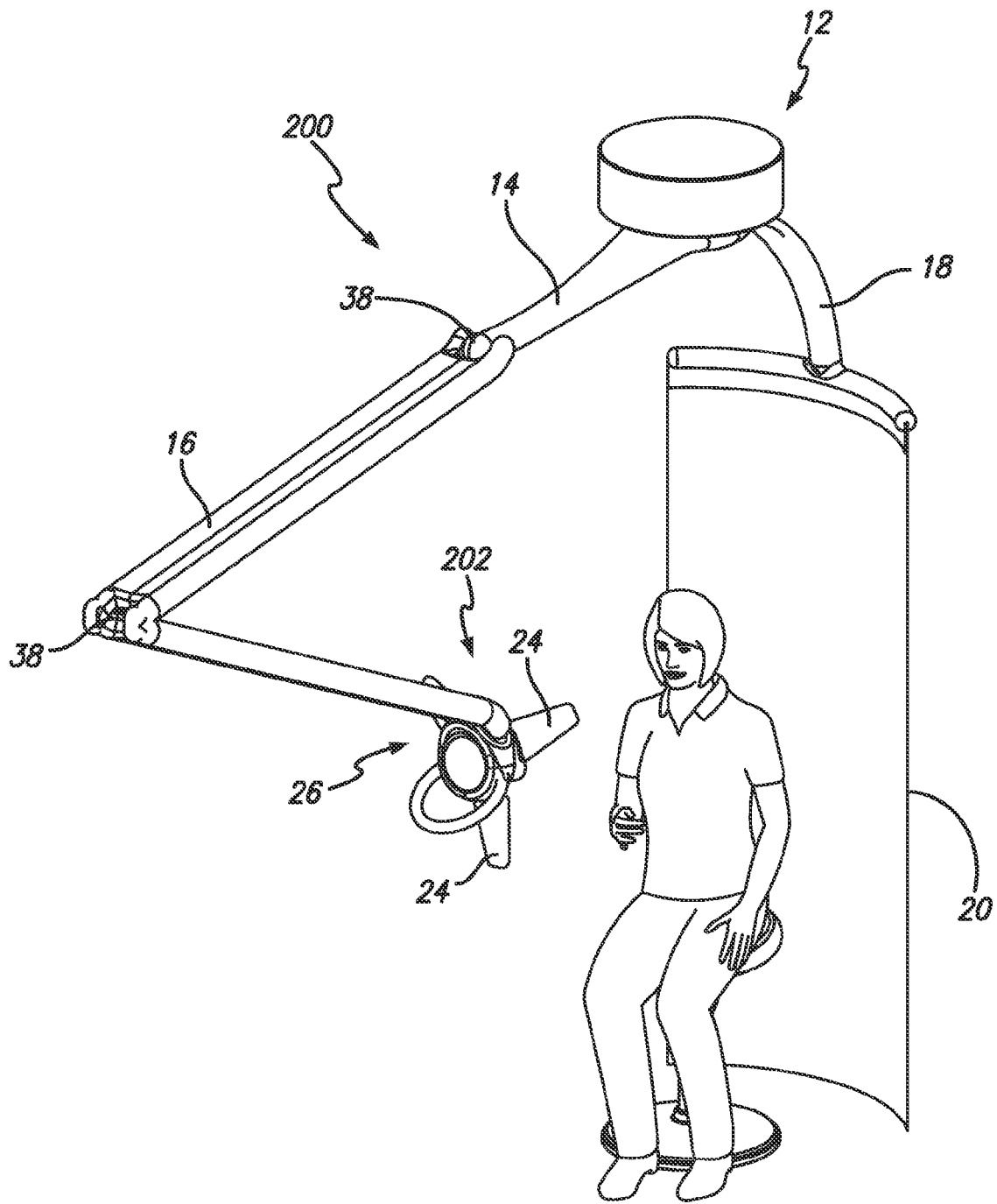
FIG. 12 is a perspective view of a 360° imaging system in accordance with a preferred embodiment of the present invention.

In a preferred embodiment, imaging system is used to capture and compare pre-surgical (or pre-event) images to post-surgical (or post-event) images of patients undergoing cosmetic procedures. Preferably, the image capturing system is configured to produce video as synchronized orbital shots of the patient. See, e.g., the images in FIGS. 11A-11C, which show a series of before and after images at different stages of a 360° rotation. Therefore, the viewer can see two rotating images next to each other that rotate in synchrony as a result of the images captured by the 360° imaging system.

Figure 13:
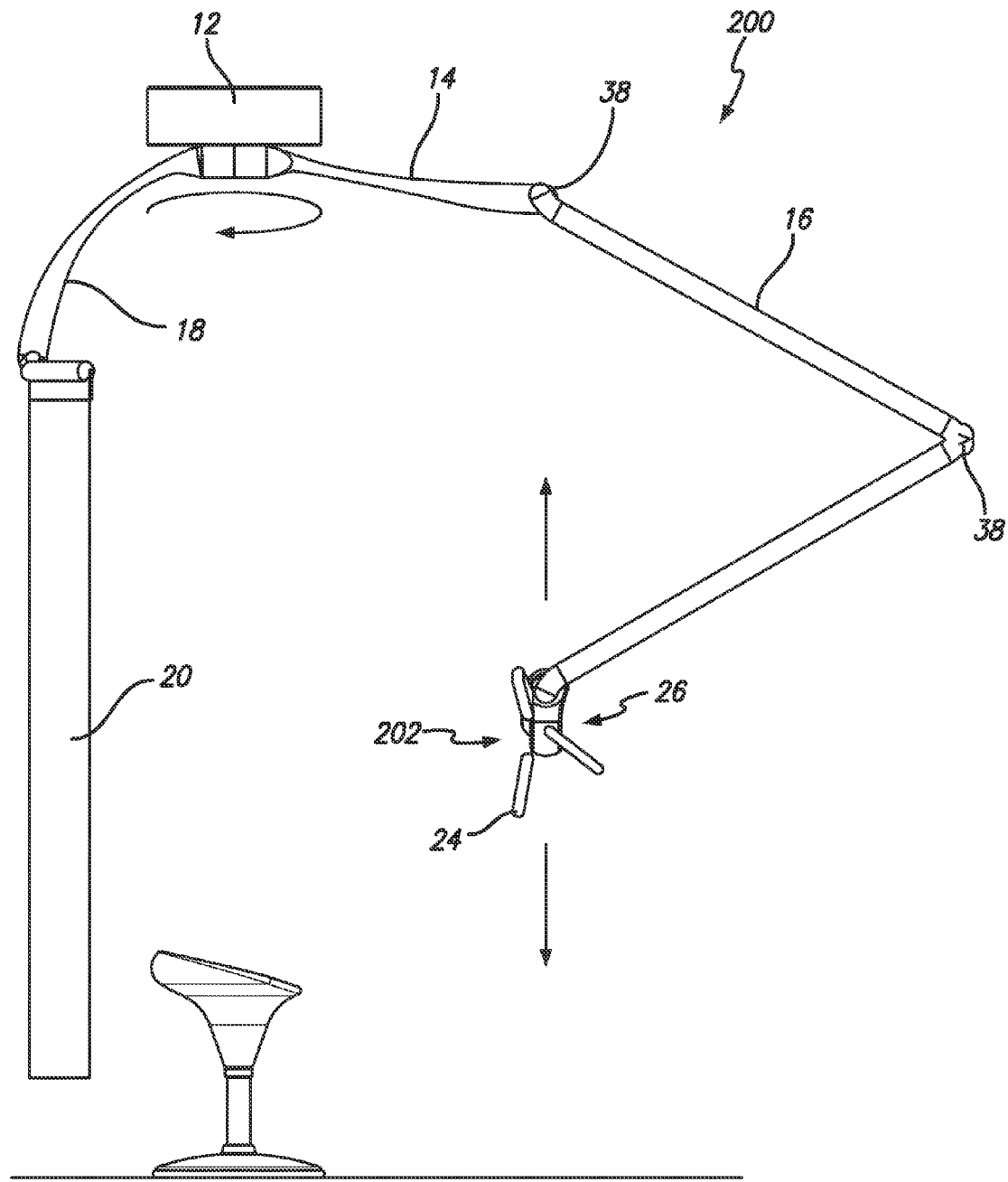
FIG. 13 is a side elevational view of the 360° imaging system of FIG. 12.
Figure 14:
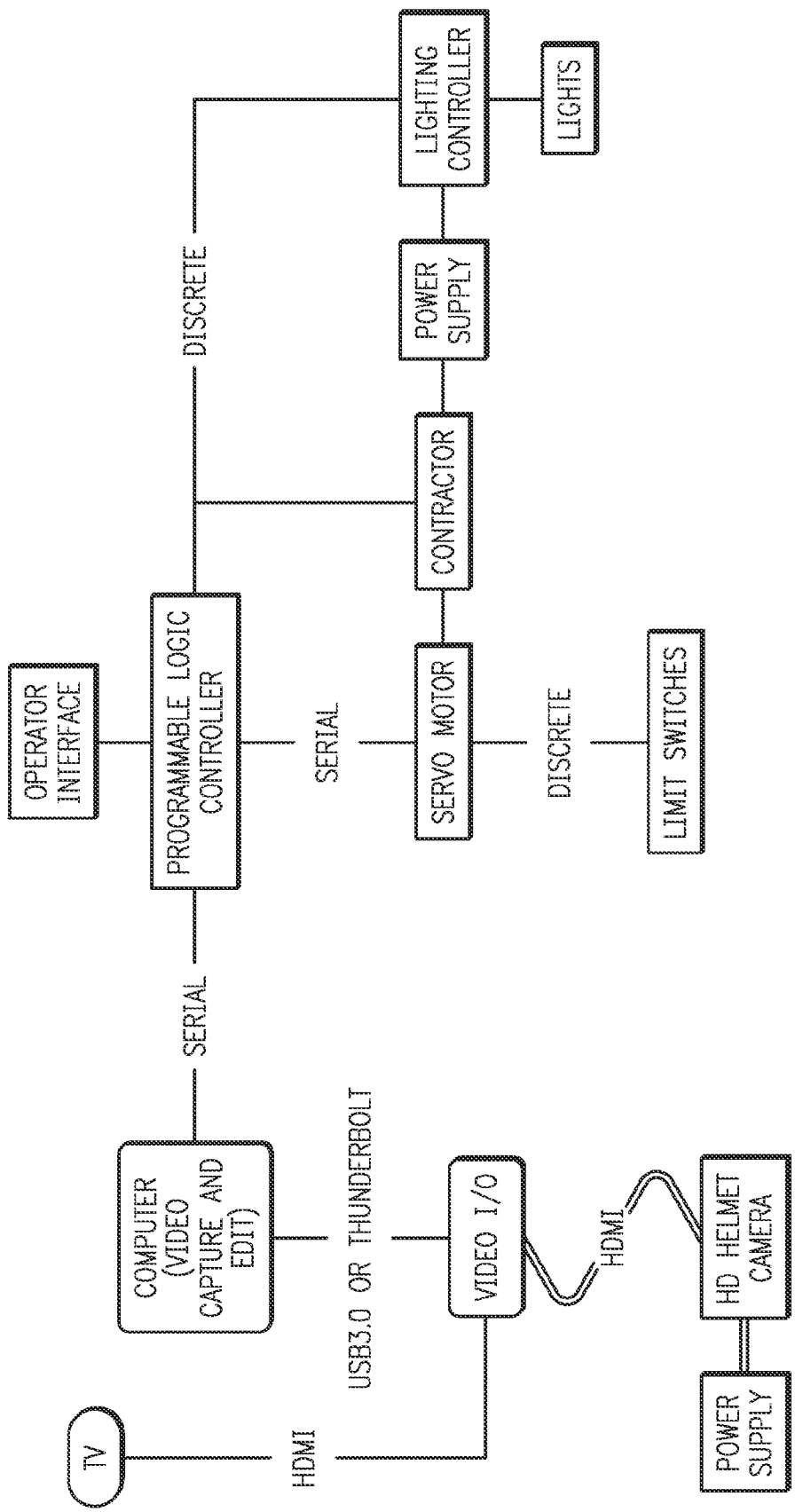
FIG. 14 is a flow diagram of exemplary electrical equipment used with the 360° imaging system of FIG. 12.
Figure 15:
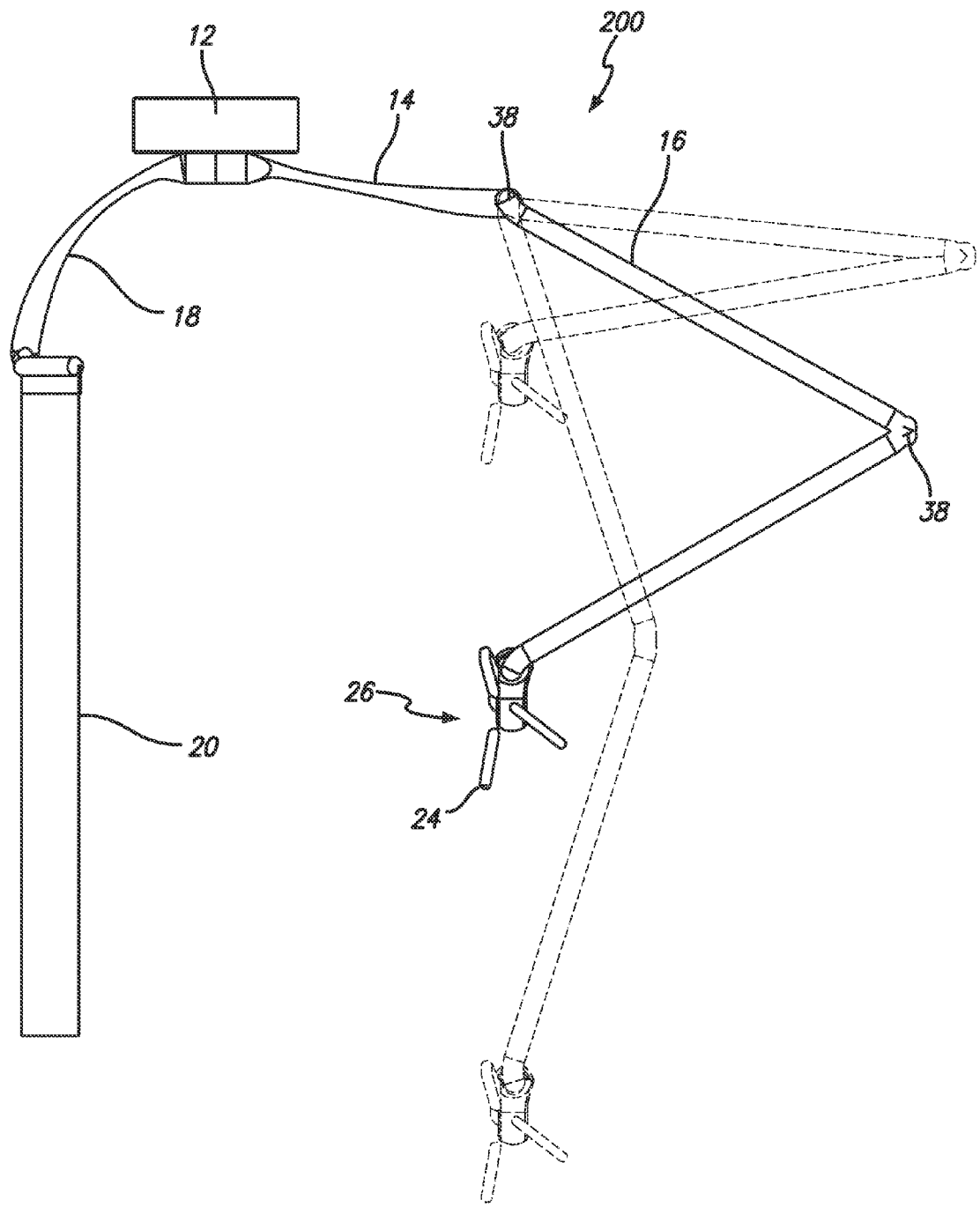
FIG. 15 is a side elevational view of the 360° imaging system of FIG. 12 showing the range of motion of the horizontal boom.

FIGS. 12-15 show another preferred embodiment of a 360° imagining system 200. Generally, the system 200 includes an upper boom 14, first and second downwardly extending vertical arms 16 and 18, backdrop 20 and camera or imaging device 26. As is shown in FIGS. 13 and 15, first downwardly extending vertical arm 16 includes joints or pivotal adjustment members 38 that allow camera or imaging device 26, and the assembly 202 in which it is housed, along with the lights 24, to movable upward and downwardly or toward or away from the subject to be imaged.

The 360° imaging system can be used in many different settings. For example, the system can be used by a dermatologist or other doctor to image a patient's skin to capture before and after images to observe changes over time in moles and other skin conditions. The system can also be used in a retail setting (e.g., a dressing room in a store) to allow a shopper to obtain a 360° image of the shopper wearing an outfit, shirt, pants, hat, etc. In this embodiment, the system can include means for downloading the image to a memory device, such as a flash drive, thumb drive, the shopper's phone, etc. This can be done wirelessly or via a data connection such as a USB or other known connection.

Figure 16:
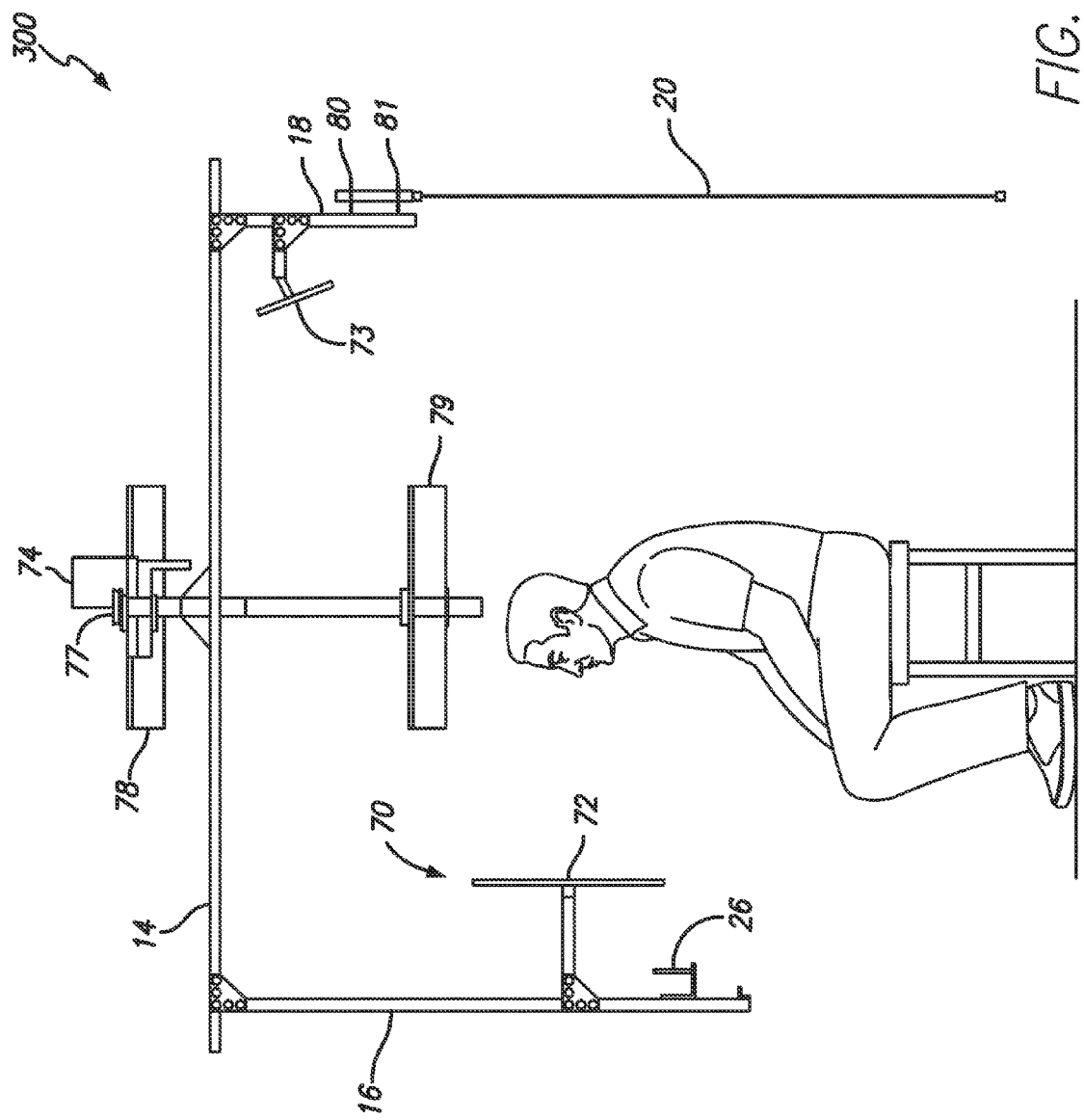
FIG. 16 is a side elevational view of a 360° imaging system in accordance with a preferred embodiment of the present invention.
Figure 17:
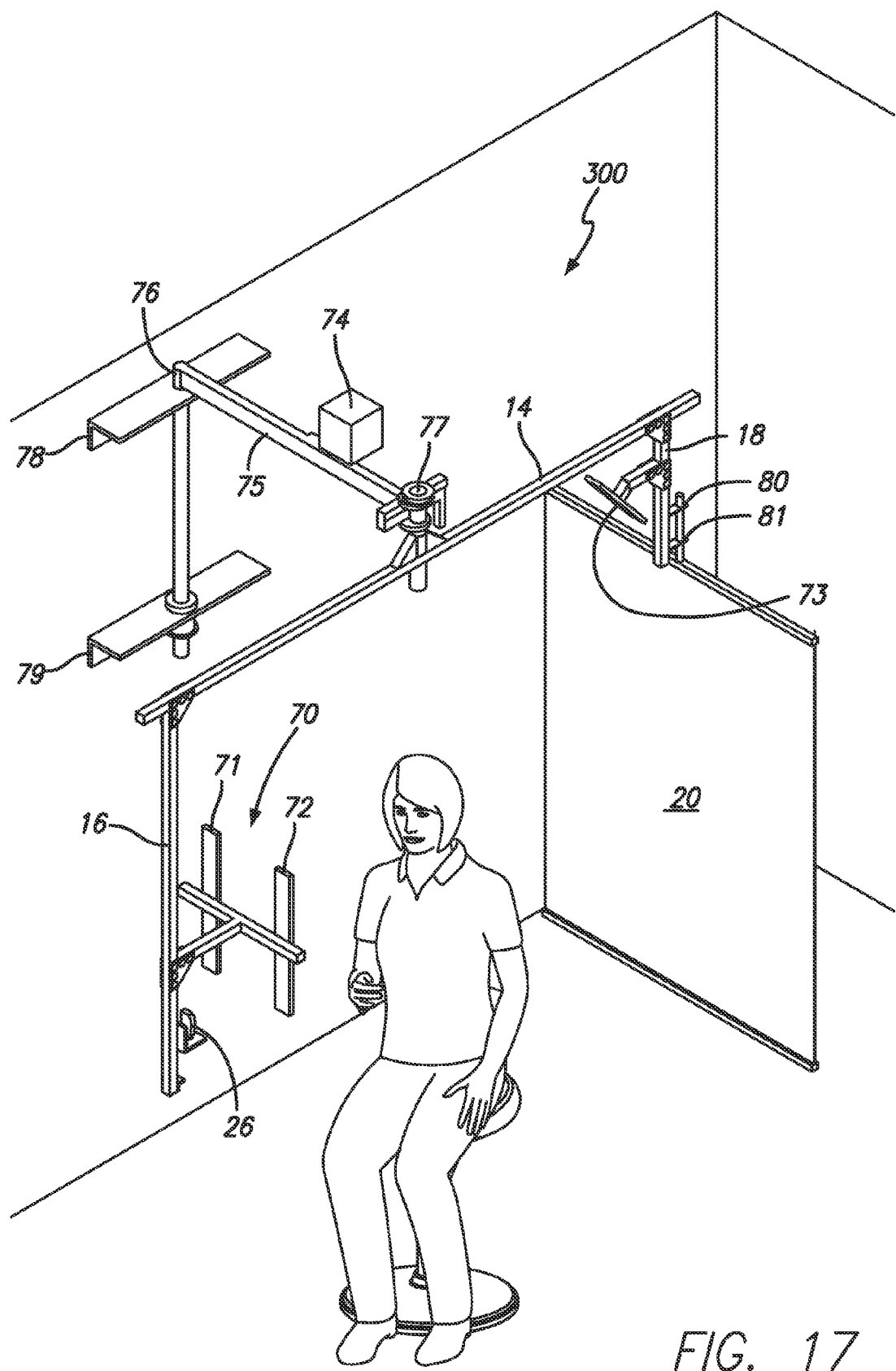
FIG. 17 is a perspective view of the 360° imaging system of FIG. 16.
Figure 18:
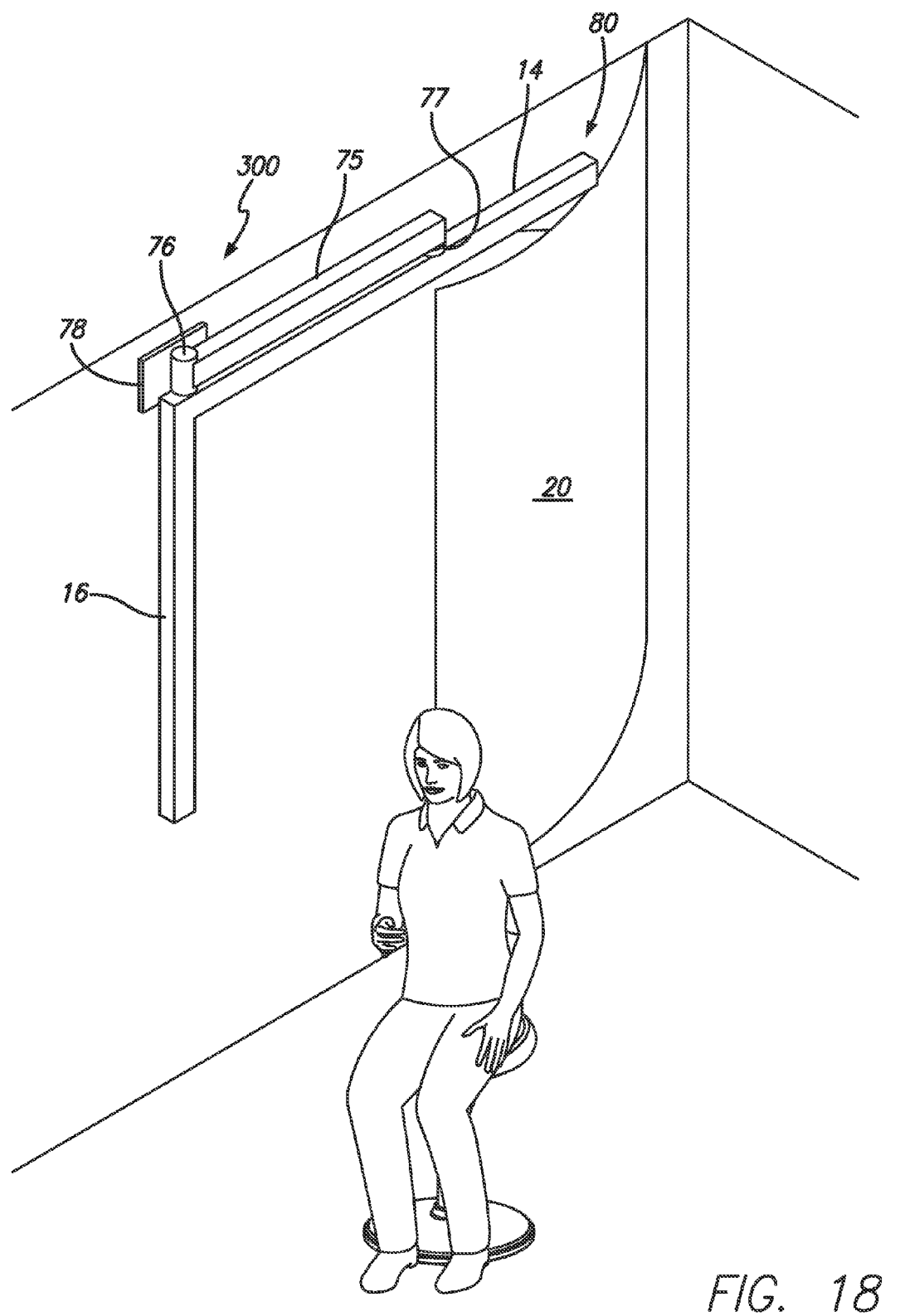
FIGS. 18 and 19 are a series of images showing fold-out and deployment movement of a 360° imaging system in accordance with a preferred embodiment of the present invention.

FIGS. 16-19 show another preferred embodiment of a 360° imaging system 300 that can fold flat or nearly flat against a wall or other surface when not in use (as depicted in FIG. 18). Generally, the system 300 includes a first horizontal boom 14, first and second vertical arms 16 and 18, backdrop 20, and camera 26. The system 300 is intended to be mounted to a wall, floor, or ceiling of a room or other fixture by way of mounting brackets 78 and 79. A single mounting bracket also may be used (as depicted by mounting bracket 78 in FIGS. 18 and 19). One end of a second horizontal boom 75 connects to mounting bracket 78 by way of a rotatable pivot 76, and the other end of the second horizontal boom 75 connects to the first horizontal boom 14 by way of another rotatable pivot 77, as can be seen in FIGS. 16-19. Camera 26 is intended to be a video camera, though it is contemplated that camera 26 could equally be a still camera, or any other imaging device known to a person of ordinary skill in the art (including any and all general or specific imaging devices discussed herein with respect to other embodiments). Moreover, multiple cameras (in any combination of video cameras, still cameras, or other imaging devices known to persons of skill or as discussed herein with respect to other embodiments), are contemplated and intended to be within the scope of the present invention.

Figure 19:
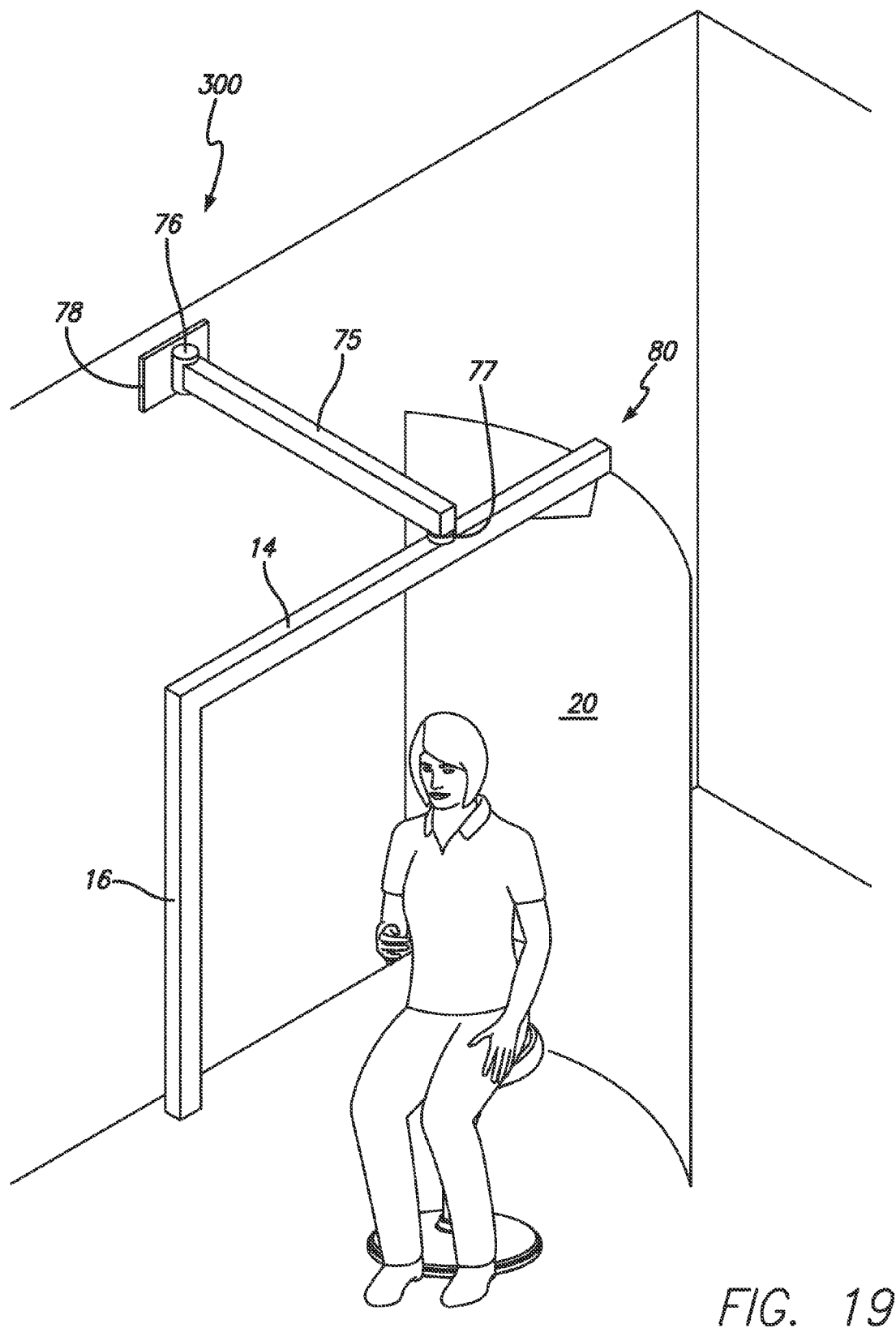

The system 300 includes a front lighting system 70, which includes lights 71 and 72. The system 300 includes a back fill light 73, which may be set at any angle, but is shown at a preferred angle of approximately 45 degrees. Backdrop 20, which may be flat (as depicted in FIGS. 16-17) or curved (as depicted in FIGS. 18-19), is attached to vertical arm 18 by way of pivots 80 and 81. It is contemplated that backdrop 20 may be attached to vertical arm 18 by way of a single pivot or any other fastening device or devices known to a person of ordinary skill in the art. Backdrop 20 also may be attached directly to first horizontal boom 14 by way of one or more pivots or other fastening device(s) known to a person of ordinary skill in the art.

In a preferred embodiment, the system 300 includes a motor system 74, which is preferably an electric motor, as shown in FIGS. 16 and 17. When the system 300 is not being used, it can be stored flat or nearly flat against a wall, as shown in FIG. 18. When the system 300 needs to be used, motor system 74 operates to swing the second horizontal boom 75 to a position that is essentially perpendicular to the mounting bracket 78, and concurrently, motor system 74 operates to swing the first horizontal boom 14 into a position that is essentially parallel to the mounting bracket 78. The movement of the first horizontal boom 14 in this manner is depicted in FIGS. 18 and 19. Because the backdrop is mounted on one or more pivots (80 and/or 81), it is capable of rotating such that its plane becomes generally parallel to a patient's back when a patient is seated (as shown in FIGS. 16, 17, and 19). The movement of the backdrop 20 in this manner is depicted in FIGS. 18 and 19. Once the system 300 is placed into its operational position (shown in FIGS. 16, 17, and 19), motor system 74 causes the first horizontal boom 14 to rotate about the second rotatable pivot 77, while camera 26 captures images at a frequency and quality that can vary or be adjusted by the operator. In another embodiment, the movement of the first horizontal boom 14 and backdrop 20 can be achieved by hand or manual movement, without the use of a motor.

The operation and uses of system 300 are similar or identical to the operation and uses of the other preferred embodiments described and discussed herein, including for the purpose of capturing images before and after surgery or other medical procedures, such that the resulting images are standardized or taken under exactly the same conditions. Accordingly, because the lighting system 70 and backfill light 73 travel with the camera 26, the before and after images that can be captured are relatively consistent. Moreover, in order to standardize photographs, the system 300 may include a color scale light emitter, standing alone or directly connected to system 300, which allows for the standardization of color as among original and subsequent photographs. The system 300 also may include an LED (light emitting diode) centering light, either alone or directly connected to system 300, which projects a point of light at a standardized location (e.g., straight down from above), and allows the patient and/or camera system to be situated in the same or nearly the same position, as among original and subsequent photographs or image set capture.

And likewise, in system 300, a patient or subject is positioned in between the camera 26 and the backdrop 20. The camera 26 travels in a generally circular path around the patient or subject, preferably at least 360 degrees (though any number of degrees is contemplated as being within the scope of the present invention). The camera 26 captures multiple images (preferably at least five (5), but any number is contemplated), during the time camera 26 passes around the subject and a first image set is captured. At a later point in time (such as after surgery or following a given medical procedure), the above procedure is repeated, including the placement of the subject in the approximately or exactly the same position with respect to the original camera orientation, and a second image set is captured (again, preferably at least five (5) images, but any number is contemplated). The rate of camera movement during capture of the second image set may be the same or substantially the same as the rate of camera movement during capture of the first image set. A practitioner or other medical professional can then compare the first image set to the second image set and make any number of useful determinations or analyses, including the success of the surgery or medical procedure, progress of the patient post-surgery, and the like. From the resulting image sets, side-by-side comparisons also can be produced, as depicted, for example, in FIGS. 11A, 11B, and 11C.

The particular arrangement shown in the figures and described herein is intended to be only exemplary. Various details of the invention may be changed without departing from the scope of the invention. Furthermore, the foregoing description of the preferred embodiment of the invention and best mode for practicing the invention are provided for the purpose of illustration only and not for the purpose of limitation, the invention being defined by the claims.

Unless the context clearly requires otherwise, throughout the description and the claims, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description of the Preferred Embodiments using the singular or plural number may also include the plural or singular number respectively. The word "or" in reference to a list of two or more items, covers all of the following interpretations of the word: any of the items in the list, all of the items in the list, and any combination of the items in the list.

The above-detailed description of embodiments of the disclosure is not intended to be exhaustive or to limit the teachings to the precise form disclosed above. While specific embodiments of and examples for the disclosure are described above for illustrative purposes, various equivalent modifications are possible within the scope of the disclosure, as those skilled in the relevant art will recognize. Further any specific numbers noted herein are only examples: alternative implementations may employ differing values or ranges.

Any patents and applications and other references noted above, including any that may be listed in accompanying filing papers, are incorporated herein by reference in their entirety. Aspects of the disclosure can be modified, if necessary, to employ the systems, functions, and concepts of the various references described above to provide yet further embodiments of the disclosure.

Accordingly, although exemplary embodiments of the invention have been shown and described, it is to be understood that all the terms used herein are descriptive rather than limiting, and that many changes, modifications, and substitutions may be made by one having ordinary skill in the art without departing from the spirit and scope of the invention.

What is claimed is:

1. A 360 degree camera imaging system comprising:
a first horizontal boom having a first end, a second end, and a middle section;
a second horizontal boom having a first end and a second end;
a first vertical arm having a first end and a second end;
a mounting bracket;
wherein the first horizontal boom is connected to the first end of the second horizontal boom by a first rotatable pivot proximate the middle section of the first horizontal boom and is configured to rotate about a rotation axis, and the second end of the second horizontal boom is connected to the mounting bracket;
wherein the first end of the first vertical arm is affixed to the first end of the first horizontal boom;
wherein a camera is mounted to the first vertical arm, and wherein a backdrop is positioned to rotate opposite of the camera;
an alignment system directed generally downwardly and located along the same axis as the rotation axis, wherein the alignment system includes an alignment camera that is configured to capture a first alignment image of a subject positioned generally co-axially with the rotation axis; and a first monitor on which the first alignment image is displayed.

2. The 360 degree camera imaging system of claim 1, wherein the second end of the second horizontal boom is connected to the mounting bracket by a second rotatable pivot.

3. The 360 degree camera imaging system of claim 2, wherein the backdrop is adapted to rotate by way of a third rotatable pivot.

4. The 360 degree camera imaging system of claim 1 further comprising a light mounted on the first vertical arm.

5. The 360 degree camera imaging system of claim 4 further comprising a second light mounted on the first horizontal boom.

6. The 360 degree camera imaging system of claim 1, wherein the camera is a video camera.

7. The 360 degree camera imaging system of claim 1 further comprising a second camera.

8. The 360 degree camera imaging system of claim 7, wherein the second camera is a still camera.

9. The 360 degree camera imaging system of claim 8, wherein an electric motor is affixed to the second horizontal boom.

10. The 360 degree camera imaging system of claim 9, wherein the electric motor is affixed proximate the first rotatable pivot.

11. The 360 degree camera imaging system of claim 7 wherein the second camera is mounted to the first vertical arm.

12. The 360 degree camera imaging system of claim 1, further comprising a color scale.

13. The 360 degree camera imaging system of claim 1, wherein the alignment system includes a light emitting diode centering light.

14. The 360 camera imaging system of claim 1 further comprising a motor control system that rotates the rotating unit after the first alignment is captured.

15. The 360 degree camera imaging system of claim 1 wherein the first monitor includes alignment markings thereon.

* * * * *